United States Patent [19]

Lecka-Czernik

[11] Patent Number: 5,959,081
[45] Date of Patent: Sep. 28, 1999

[54] ZINC BINDING LIM PROTEIN S2-6

[75] Inventor: Beata Lecka-Czernik, 8710 Boulder La., Little Rock, Ark. 72227

[73] Assignee: The Board of Trustees of the University of Arkansas, Little Rock, Ark.

[21] Appl. No.: 08/856,444

[22] Filed: May 14, 1997

[51] Int. Cl.⁶ .......................... A61K 38/16; C12N 15/00; C12N 5/00; C07H 21/02
[52] U.S. Cl. ...................... 530/358; 435/320.1; 435/325; 536/23.1
[58] Field of Search ................................ 435/320.1, 325; 530/358; 536/23.1

[56] References Cited

PUBLICATIONS

Divecha, N. et al., Gene, vol. 156, pp. 283–286, 1995.

*Primary Examiner*—Robert A. Wax
*Assistant Examiner*—Peter P. Tung
*Attorney, Agent, or Firm*—Benjamin Aaron Adler

[57] ABSTRACT

A substantially pure S2-6 protein (a) having a zinc binding LIM domain, (b) whose mRNA is preferentially expressed in nonproliferating or growth inhibited human diploid fibroblasts, (c) whose mRNA is overexpressed in senescent human diploid fibroblasts or human diploid fibroblasts derived from a patient with Werner Syndrome, and (c) whose mRNA expression is reduced or abolished in fetal human diploid fibroblasts, immortalized cells, cancerous cells and other highly proliferative cells.

8 Claims, 9 Drawing Sheets

```
        GTCAGCAAGAGGTGTGGCATGTTTGGGATGCAAGGGGACGTGTTCGGGCTTCGAGCACAT
   1    ---------+---------+---------+---------+---------+---------+  60
        CAGTCGTTCTCCACACCGTACAAACCCTACGTTCCCCTGCACAAGCCCGAAGCTCGTGTA

V  S  K  R  C  G  M  F  G  M  Q  G  D  V  F  G  L  R  A  H

TCATGGAGGAAAATATGCAAGTCTTGCAAATGCAGCCAAGAGGACCACTGCCTAACATCT
  61    ---------+---------+---------+---------+---------+---------+ 120
        AGTACCTCCTTTTATACGTTCAGAACGTTTACGTCGGTTCTCCTGGTGACGGATTGTAGA

S  W  R  K  I  C  K  S  C  K  C  S  Q  E  D  H  C  L  T  S  -

GACCTAGAAGACGATCGGAAAATTGGCCGCTTGCTGATGGACTCCAAGTATTCCACCCTC
 121    ---------+---------+---------+---------+---------+---------+ 180
        CTGGATCTTCTGCTAGCCTTTTAACCGGCGAACGACTACCTGAGGTTCATAAGGTGGGAG

D  L  E  D  D  R  K  I  G  R  L  L  M  D  S  K  Y  S  T  L  -

ACTGCTCGGGTGAAAGGCGGGGACGGCATCCGGATTTACAAGAGGAACCGGATGATCATG
 181    ---------+---------+---------+---------+---------+---------+ 240
        TGACGAGCCCACTTTCCGCCCCTGCCGTAGGCCTAAATGTTCTCCTTGGCCTACTAGTAC

T  A  R  V  K  G  G  D  G  I  R  I  Y  K  R  N  R  M  I  M  -

ACCAACCCTATTGCTACTGGGAAAGATCCCACTTTTGACACCATCACCTACGAGTGGGCT
 241    ---------+---------+---------+---------+---------+---------+ 300
        TGGTTGGGATAACGATGACCCTTTCTAGGGTGAAAACTGTGGTAGTGGATGCTCACCCGA

T  N  P  I  A  T  G  K  D  P  T  F  D  T  I  T  Y  E  W  A  -

CCCCCTGGAGTCACCCAGAAACTGGGACTGCAGTACATGGAGCTCATCCCCAAGGAGAAG
 301    ---------+---------+---------+---------+---------+---------+ 360
        GGGGGACCTCAGTGGGTCTTTGACCCTGACGTCATGTACCTCGAGTAGGGGTTCCTCTTC

P  P  G  V  T  Q  K  L  G  L  Q  Y  M  E  L  I  P  K  E  K  -

CAGCCAGTGACAGGCACAGAGGGTGCCTTTTACCGCCGCCGCCAGCTCATGCACCAGCTC
 361    ---------+---------+---------+---------+---------+---------+ 420
        GTCGGTCACTGTCCGTGTCTCCCACGGAAAATGGCGGCGGCGGTCGAGTACGTGGTCGAG

Q  P  V  T  G  T  E  G  A  F  Y  R  R  R  Q  L  M  H  Q  L  -

CCCATCTATGACCAGGATCCCTCGCGCTGCCGTGGACTTTTGGAGAATGAGTTGAAACTG
 421    ---------+---------+---------+---------+---------+---------+ 480
        GGGTAGATACTGGTCCTAGGGAGCGCGACGGCACCTGAAAACCTCTTACTCAACTTTGAC

```
     ATGGAAGAATTTGTCAAGCAATATAAGAGCGAGGCCCTCGGCGTGGGAGAAGTGGCCCTC
481  ---------+---------+---------+---------+---------+---------+ 540
     TACCTTCTTAAACAGTTCGTTATATTCTCGCTCCGGGAGCCGCACCCTCTTCACCGGGAG

M  E  E  F  V  K  Q  Y  K  S  E  A  L  G  V  G  E  V  A  L  -

CCGGGCAGGGTGGCTTGCCCAAGGAGGAGGGGAAGCAGCAGGAAAAGCCAGAGGGGGCAG
541  ---------+---------+---------+---------+---------+---------+ 600
     GGCCCGTCCCACCGAACGGGTTCCTCCTCCCCTTCGTCGTCCTTTTCGGTCTCCCCCGTC

P  G  R  V  A  C  P  R  R  R  G  S  S  R  K  S  Q  R  G  Q  -

AGACCACTGCTGCTACCACCAACGGCAGTCTCAGTGACCCGTCCAAAGAAGTGGAATACG
601  ---------+---------+---------+---------+---------+---------+ 660
     TCTGGTGACGACGATGGTGGTTGCCGTCAGAGTCACTGGGCAGGTTTCTTCACCTTATGC

R  P  L  L  P  P  T  A  V  S  V  T  R  P  K  K  W  N  T  -

TCTGCGAGCTCTGCAAGGGAGCGGCCCCTCCTGACAGCCCCGTGGTCTACTCGACAGGGC
661  ---------+---------+---------+---------+---------+---------+ 720
     AGACGCTCGAGACGTTCCCTCGCCGGGGAGGACTGTCGGGGCACCAGATGAGCTGTCCCG

S  A  S  S  A  R  E  R  P  L  L  T  A  P  W  S  T  R  Q  G  -

AGGCTACAACAAGCAGTGGCACCCCACCTGCTTTGTGTGTGCCAAGTGCTCCGAGCCGCT
721  ---------+---------+---------+---------+---------+---------+ 780
     TCCGATGTTGTTCGTCACCGTGGGGTGGACGAAACACACACGGTTCACGAGGCTCGGCGA

R  L  Q  Q  A  V  A  P  H  L  L  C  V  C  Q  V  L  R  A  A  -

GGTGGACCTCATCTACTTCTGGAAGGATGGTCACCCTGGTGCGGCCGCCATTACTGCGAG
781  ---------+---------+---------+---------+---------+---------+ 840
     CCACCTGGAGTAGATGAAGACCTTCCTACCAGTGGGACCACGCCGGCGGTAATGACGCTC

G  G  P  H  L  L  E  G  W  S  P  W  C  G  R  H  Y  C  E  -

AGTCTGCGGCCCCGGTGCTCCGGCTGCGATGAGATAATATTCGCTGAGGACTACCAGCGT
841  ---------+---------+---------+---------+---------+---------+ 900
     TCAGACGCCGGGGCCACGAGGCCGACGCTACTCTATTATAAGCGACTCCTGATGGTCGCA

S  L  R  P  R  C  S  G  C  D  E  I  I  F  A  E  D  Y  Q  R  -

GTGGAAGATCTGGCCTGGCACCGAAAGCACTTTGTCTGTGAGGGTTGTGAGCAGCTGCTG
901  ---------+---------+---------+---------+---------+---------+ 960
     CACCTTCTAGACCGGACCGTGGCTTTCGTGAAACAGACACTCCCAACACTCGTCGACGAC

V  E  D  L  A  W  H  R  K  H  F  V  C  E  G  C  E  Q  L  L  -

AGCGGCCGGGCGTACATCGTCACCAAGGGTCAGCTTCTGTGCCCAACTTGCAGCAAGTCC
961  ---------+---------+---------+---------+---------+---------+ 1020
     TCGCCGGCCCGCATGTAGCAGTGGTTCCCAGTCGAAGACACGGGTTGAACGTCGTTCAGG

```
           AAACGCTCCTGAAGGGCTGCCCACCCACAGCCAGAATCCACAGGATCCCACCGAGAAGGA
    1021   ---------+---------+---------+---------+---------+---------+  1080
           TTTGCGAGGACTTCCCGACGGGTGGGTGTCGGTCTTAGGTGTCCTAGGGTGGCTCTTCCT

K   R   S   *

GCCAGGTGTGCCGAGACCATCCTAAGGGTCCGATGTGACAGCAAGCAAGTGAATAAACAA
    1081   ---------+---------+---------+---------+---------+---------+  1140
           CGGTCCACACGGCTCTGGTAGGATTCCCAGGCTACACTGTCGTTCGTTCACTTATTTGTT

TGATTTGCTTTTCAGTGAGAATATATATATGAGATATATATAGATATATATCTAGGTTGG
    1141   ---------+---------+---------+---------+---------+---------+  1200
           ACTAAACGAAAAGTCACTCTTATATATATACTCTATATATATCTATATATAGATCCAACC

GTGGTGGTAGATCCTTGAGGGTCAGTAGTTTCAAAACCAAAAATATTCTAAGAAGTCTTA
    1201   ---------+---------+---------+---------+---------+---------+  1260
           CACCACCATCTAGGAACTCCCAGTCATCAAAGTTTTGGTTTTTATAAGATTCTTCAGAAT

GGATGGAGTTCCTTTTCTTTCTGTTGTTGTTTCCCAGCTACAACCAACTAAAGACACAAA
    1261   ---------+---------+---------+---------+---------+---------+  1320
           CCTACCTCAAGGAAAAGAAAGACAACAACAAAGGGTCGATGTTGGTTGATTTCTGTGTTT

TGGCGTTCTGCAAGGGGACTCTGGGAGGAGTTTTCCAGAATGCAATTCCGAGTGAGCAAA
    1321   ---------+---------+---------+---------+---------+---------+  1380
           ACCGCAAGACGTTCCCCTGAGACCCTCCTCAAAAGGTCTTACGTTAAGGCTCACTCGTTT

TCGCATAGCTGTAGAATGTGCGTGCTTTTTGTGGACACAGGAGCTCCTCCAGGAGCAGG
    1381   ---------+---------+---------+---------+---------+---------+  1440
           AGCGTATCGACATCTTACACGCACGAAAAACACCTGTGTCCTCGAGGAGGTCCTCGTCC

CTGGGATCCCAACTATCGCTTGTTGCCTCTTTTTCAAGTGGAATTTGAATTTTAAATAAA
    1441   ---------+---------+---------+---------+---------+---------+  1500
           GACCCTAGGGTTGATAGCGAACAACGGAGAAAAAGTTCACCTTAAACTTAAAATTTATTT

CAACTTTTTTTGGCATGATAAACAGATCAATAAAAGTTTTGTGAATTCC
    1501   ---------+---------+---------+---------+---------   1549
           GTTGAAAAAAACCGTACTATTTGTCTAGTTATTTTCAAAACACTTAAGG
```

FIG. 2C

```
TESTIN   1  CPRCGQAVYAAEKVIGAGKSWHKSCFRCAKCGKSLESTTLADKDGEIYCKGC
         2  CAGCDELIFSNEYTQAENQNWHLKHFCCFTCDHILAGKIYVMVTDKPVCKRC
HIC-5       CGSCNKPI-AGQVVTALGRAWHPEHFLCSGCSTTLGGSBFFEKDGAPFCPEC
S2-6        CSGCDEIIFAEDYQRVEDLAWHRKHFVCEGCSQLLSGRAYIVTKGQLICPIC
                            *     *      *
```

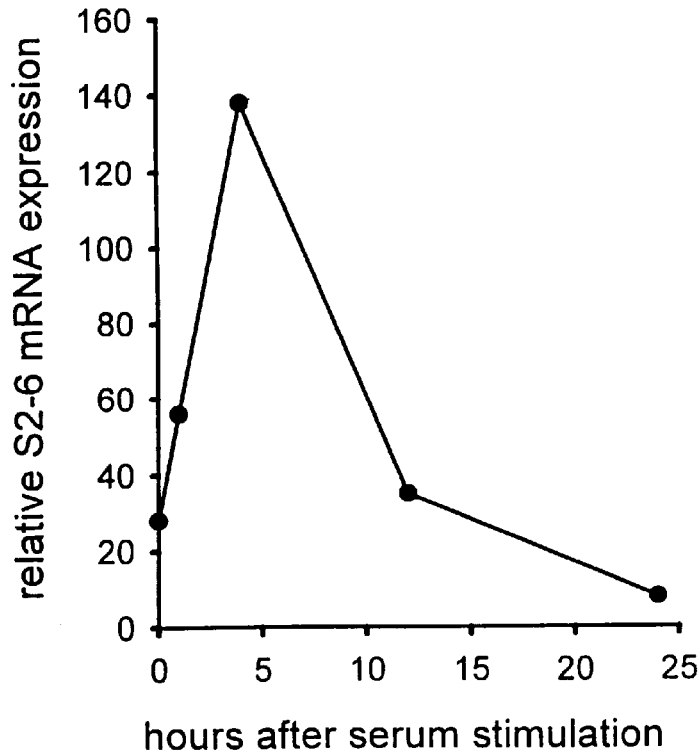
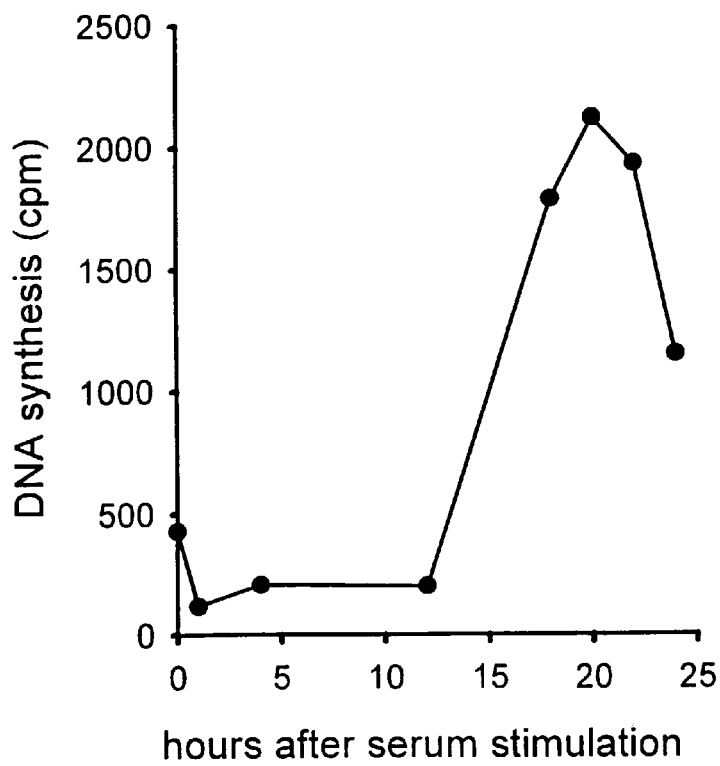
FIG. 6B

```
S1-3        VFRCDKCTFT-CSSDES---LQQHIEK-HNELK
            PYKCQLCYYE-TKHTEE---LDSHLRNEHKVSR
            RFPCEFCGRA-FSQGSE---WERHVLR-HGMAL hunchback   PFQCDKCSYT-CVNKSM---LNSHRKS-HSSVY
            PFRCIICGRS-FLWSSY---LRVHMRI-HTGEK mKr3        PYVCQYCGKA-FTEHSG---LNKHLRK-HTGEK
            SHRCGDCGKG-FAWASH---LQRHRRV-HTGER cKr1        PFPCGLCGER-FSQKAH---LLQHGKT-HRPER
            PYECPECGEA-FSQGSH---LTKHRRS-HGPKA

S2-6        RPRCSGCDEIIFAFAEDYQRLAWHRK--HFVCE
```

FIG. 7

ZINC BINDING LIM PROTEIN S2-6

FEDERALLY FUNDING LEGEND

This invention was made at least in part with funds from the Federal Government, under the Arkansas Experimental Program to Stimulate Competitive Research funded by the National Science Foundation, the Arkansas Science and Technology Authority and the University of Arkansas for Medical Sciences.

BACKGROUND OF THE INVENTION

1. Field of the Invention

This invention relates generally to molecular biology and the inhibition of DNA synthesis. More specifically, the present invention relates to a new zinc binding LIM domain protein designated S2-6.

2. Description of the Related Art

Biological aging, an inevitable process common to multicellular organisms, involves a progressive physiological decline and associated pathologic degeneration of tissues and organs. The fundamental basis of aging remains enigmatic (Goldstein, 1992; Dice, 1993). The discovery that human diploid fibroblasts (HDF) have a finite proliferative lifespan opened the way to explore aging at the cellular level (Hayflick, 1965). The major feature of senescent HDF is their inability to synthesize DNA due to Gl arrest and failure to traverse the Gl/S boundary (Goldstein, 1990; Cristofalo and Pignolo, 1993). A further hallmark of senescence is the dominant effect of the senescent nucleus on DNA synthesis in the young nucleus, as demonstrated in experiments involving somatic cell fusions between young and old cells. Initiation of DNA synthesis in the young HDF nucleus was extinguished, but ongoing DNA synthesis was not (Norwood et al., 1974; Stein and Yanishevsky, 1981). Moreover, this effect is reduced by blockers of RNA and protein synthesis indicating that inhibition of DNA synthesis depends upon one or more proteins and perhaps on a direct inhibitory action of RNA(s) (Norwood et al., 1990).

Human diploid fibroblast cells (HDF) cultured in vitro provide an excellent model system for the study of biologic aging (Hayflick 1965; Goldstein 1990). These cells possess a limited replicative lifespan ("senescence in vitro"), that can be measured as the $MPD_{max}$, the maximum number of Mean Population Doublings accruing until phaseout. However, the great majority of senescent cells remain viable and capable of carrying out all metabolic and macromolecular functions except semiconservative DNA synthesis.

In several large series of HDF cultures, the $MPD_{max}$ is inversely proportional to the age of the donor. Moreover, HDF from subjects with Werner syndrome (WS) display a sharply curtailed growth capacity compared to age-matched controls (Thweatt, et al. 1993). Thus, physiologic rather than chronologic age determines the $MPD_{max}$, and HDF clearly count cell divisions, rather than calendar or metabolic time, to a critical limit (Goldstein 1990; Goldstein 1989). That the replicative lifespan of cultured fibroblasts from a diversity of animal species is directly proportional to the maximum life expectancy of these species (2–150 years) indicates the presence of powerful genetic determinants of cellular senescence (Goldstein 1990; Goldstein 1992). Thus, the data suggest a critical connection between senescence of HDF in vitro and biologic aging in vivo.

Dominance of the senescent phenotype in HDF

Cell fusion experiments have guided the search for root causes of HDF senescence. In repeated attempts at forming proliferating cell hybrids, young HDF (yHDF) failed to rescue senescent HDF (sHDF) after cell fusion, but permanent cell lines were able to do so (Goldstein, 1971). In short-term cell hybrids containing a senescent and a young nucleus within a single cytoplasm, i.e. heterocaryons, initiation of DNA synthesis in the yHDF nucleus was extinguished (Goldstein, 1971) but ongoing DNA synthesis was not (Yanishevsky, et al. 1980; Norwood, et al. 1990). Brief post-fusion treatment of such heterocaryons with blockers of RNA and protein synthesis abrogated the inhibition (Norwood, et al. 1990). Thus, these data indicate that senescence is a dominant trait mediated by proteins or perhaps RNAs. In strong support of this concept, Lumpkin, Smith and co-workers microinjected polyA$^+$RNA from sHDF into yHDF and were able to inhibit DNA synthesis (Lumpkin, et al. 1986).

Relationship between HDF senescence and negative growth regulation

The primary mechanism by which senescent cells irreversibly lose the ability for transit through the Gl/S checkpoint of the cell cycle, which differentiates them from growth arrested (quiescent) cells, is unclear. Quiescence (arrested) and senescence share many proteins in common whose activity lead to the inhibition of DNA synthesis. Recently discovered proteins controlling cell cycle progression belong to this category. Their function is to inhibit activity of cyclin dependent kinase-cyclin (CDK-cyclin) complexes. These proteins are termed CDK inhibitory proteins (CKIs) and appear to be responsible for braking the cell cycle. Some of these proteins are activated in response to extracellular signals, while others appear to function intrinsically during the cell cycle (reviewed in Hunter 1993 and Peters, et al. 1994).

The p21 protein was initially identified by functional cloning of a gene sequence (SDI1) coding for an inhibitor of DNA synthesis and is overexpressed in sHDF at a level approximately 10–20 times the level seen in yHDF (Noda, et al. 1994). The identical protein was discovered virtually simultaneously by investigating systems unrelated to senescence p21 and another protein were isolated by their ability to bind and inhibit Cdk2-cyclin A and Cdk2-cyclin E complexes activities (Xiong, et al. 1993; Harper 1993), and WAF1 was induced by p53 protein in response to DNA damage, leading to transient cell cycle arrest by inhibiting CDKs (El-Deiry, et al. 1993; Dulic, et al. 1994).

Another negative regulator of cell cycle transit named p16, identified by its association with Cdk4 in the yeast two-hybrid protein interaction system, appears to specifically inhibit Cdk4-cyclin D kinase activity in vitro (Serrano, et al. 1993). A major target of this kinase seems to be the retinoblastoma product (Rb), which must be phosphorylated for proper progression through Gl phase. Data support the proposal that p16 prevents phosphorylation of Rb (Serrano, et al. 1993). Closely related studies, primarily by Stein and co-workers, have analyzed the role of Rb in HDF senescence. Following serum stimulation Rb remains underphosphorylated in sHDF, in contrast, phosphorylated Rb is abundant following serum stimulation of quiescent (arrested) yHDF (Stein, et al. 1990). Moreover, underphosphorylated Rb in sHDF is associated with the failure to express Cdc2, cyclin A and cyclin B (Stein, et al. 1991; Richter, et al. 1991), the inability to phosphorylate the Cdk2-cyclin E complex (despite its elevated protein level), and the attenuation of Cdk2-cyclin D1 and Cdc2-cyclin A complexes activities (Dulic, et al. 1993). The intrinsic cell cycle machinery is controlled by external signals such as growth factors and anti-mitogens which allows for coordination of cell division with environmental and developmental stimuli. TGF which can exhibit anti-mitogenic activity (Moses, et al. 1990) plays a role in expression of certain mRNAs and proteins like fibronectin, type(I) collagen, thrombospondin and SPARC/osteonectin (Penttinen, et al. 1988; Reed, et al. 1994), which are overexpressed in sHDF and WS HDF (Murano, et al. 1991), and also has been associated with the inhibition of the Cdk2-cyclin E complex kinase activity (Koff, et al. 1993). The protein responsible for this inhibition, p27, recently has been identified as associated with the Cdk2-cyclin E complex in cells arrested by TGF-_ (Polyak, et al. 1994; Polyak, et al. 1994; Toyoshima, et al. 1994). p27 appears to be involved in cell cycle arrest imposed by contact inhibition (Polyak, et al. 1994).

Senescing cells undergo changes which suggest altered transcriptional regulation of gene expression. Because transcription factors are attractive candidates which may ultimately specify the senescent phenotype, many studies have been performed to describe the expression and activity of known transcription factors in senescent cells. These studies revealed that E2F transcription factor which is a positive regulator of several late Gl phase genes required for Gl/S transition, is underexpressed in senescent cells and its activity is negatively regulated by the unphosphorylated form of Rb (Dimri, et al. 1994; Nevins 1992; Flemington, et al. 1993). Moreover in sHDF genes coding for transcription factors involved in the immediate early response to growth factors such as c-fos, Id-1h and Id-2h, appear to be irreversibly repressed (Dimri, et al. 1994; Seshadri, T. et al. 1990; Riabowol, et al. 1992; DeTata, et al. 1993; Hara, et al. 1994) or their binding activity is changed (Dimri, et al. 1994). However, there is a paucity of information about transcription factors as positive regulators of genes involved in inhibition of DNA synthesis and cell proliferation. Indeed a transcription factor specific for or overexpressed in senescent cells, has yet to be identified.

An important new family of proteins, the LIM protein family, has recently been described with roles in developmental and cell growth regulation. The LIM protein family, named for three of the originally identified protein members, lin-11 (Freyd, et al. 1990), isl-1 (Karlsson, et al. 1990), and mec-3 (Way, et al. 1988), is defined by the presence of one to three repeats of a 52-residue segment containing two adjacent zinc binding domains separated by a two-residue linker $(CX_2CX_{17}HX_2C)-X_2-(CX_2CX_{17}CX_2C/H/D)$. Although the LIM domain consists of two "zinc finger" domains, a controversy still remains about its DNA binding activity (Sanchez-Garcia, et al. 1994). Several studies indicate that it serves rather as a protein binding interface (Schmeichel, et al. 1994).

The LIM family consists of a variety of proteins with diverse functions and subcellular distributions; it includes transcription factors, protooncogene products and components of adhesion plaques. Based on the protein structure one can categorize the LIM family into three different groups. First, proteins containing a DNA binding homeodomain and a transcription activation domain adjacent to the LIM domains. This subfamily includes transcription factors involved in cell fate determination and differentiation as lin-11, isl-1 and mec-3. The second group, named "LIM-only" proteins, consists of several members that do not contain any additional known functional domains except LIM domains. LIM-only proteins appear to be involved in the regulation of gene activity even if they do not bind to DNA themselves. This group includes among others the protooncogene rhombotin-1, focal adhesion protein zyxin, cysteine-rich intestinal protein CRIP (Sanchez-Garcia, et al. 1994) and three newly discovered proteins with roles in the control of cell proliferation. MLP-muscle LIM protein plays a role in muscle differentiation by driving undifferentiated cells out of the cell cycle, a crucial step for initiation of the differentiation process (Arber, et al.). The protein ril was isolated from a revertant of ras-transformed cells and seems to be involved in the maintenance of normal cell growth (Kiess, et al. 1995). This gene is expressed in a variety of normal differentiated cells but is down-regulated in ras-transformed cells suggesting its function as a negative growth regulator. Another member of the LIM-only group, hic-5 protein was originally isolated from a mouse osteoblastic cell line whose growth was inhibited by TGF-$\beta$1 (Shibanuma, et al. 1994). Hic-5 expression is also repressed in ras-transformed fibroblasts as well as in several cell lines established from human tumors. Its transcript accumulates during senescence in vitro and its overexpression is driven by the cytomegalovirus promoter which suggests that hic-5 has a cytostatic effect on cell growth (Shibanuma, et al. 1994). Third, a group of proteins which in addition to LIM domains also contain a protein kinase activity, is represented by two members: Kiz-1, with a role in cell proliferation and neuron differentiation (Bernard, 1994), and LIMK specific for lung tissue. The specific function for both proteins is not yet known, but there is evidence for their nuclear localization.

Werner syndrome (WS) provides an excellent model for the study of aging because it is a genetically-determined syndrome with features of premature aging (Thweatt, et al. 1993; Goldstein 1978; Salk 1982). The multifaceted pathology that occurs sporadically during aging of normal persons appears almost universally in WS subjects, which becoming manifest earlier and with greater severity. Without exception, HDF derived from WS subjects display a curtailed replicative lifespan and also yield a dominant inhibition of DNA synthesis in hybrid cell fusions with normal yHDF (Salk 1982; Tanaka, et al. 1980). The in vitro observations lead to the prediction that the genes responsible for inhibition of DNA synthesis should be overexpressed in WS cells (Murano, et al. 1991; Goldstein, et al. 1989).

The prior are is deficient in the lack of a new zinc binding LIM adomain protein designated S2-6. The present invention fulfills this longstanding need and desire in the art.

SUMMARY OF THE INVENTION

In general, a novel polypeptide, designated S2-6, is identified and characterized. S2-6 cDNA clone, isolated from cells undergoing a process of premature senescence, codes for a novel protein which contains a specific zinc binding LIM domain (Group 2 of the LIM family). The 1.5 cDNA partial insert of clone S2-6 has been entirely sequenced and has been shown to code for a new member of the LIM protein family. The putative protein deduced from the cDNA sequence contains a cysteine-rich zinc binding LIM domain on its C-terminus.

S2-6 clone was identified during the screening of a Werner syndrome cDNA library for overexpressed genes that may be involved in senescence of human fibroblasts. The S2-6 cDNA clone codes for a novel LIM protein, expressed specifically in nonproliferating, growth arrested cells, with a function in inhibition of DNA synthesis. The S2-6 mRNA is exclusively expressed in nonproliferating normal cells and is not expressed in immortal cells. Moreover, microinjection of S2-6 antisense partial mRNA into nonproliferating human fibroblasts stimulates DNA synthesis which indicates S2-6 role in inhibition of DNA synthesis. S2-6 protein may be an inhibitor of DNA synthesis in nonproliferating cells. Thus, the S2-6 gene sequence may play a role in regulation of cell growth and differentiation. Strategies of overexpressing S2-6 protein in cancerous cells may lead to inhibition of cell growth that is important in anti-cancer therapy.

The invention includes a substantially pure DNA encoding a DNA binding protein, a strand of which DNA will hybridize at high stringency to a probe containing a sequence of at least 15 consecutive nucleotides of FIG. 2 (SEQ ID NO: 1; human S2-6). The protein encoded by the DNA of the invention may share at least 80% sequence identity (preferably 85%, more preferably 90%, and most preferably 95%) with the amino acids listed in FIG. 2 (SEQ ID NO: 2.). More preferably, the DNA includes the coding sequence of the nucleotides of FIG. 2 (SEQ ID NO: 1; human S2-6 cDNA), or a degenerate variant of such a sequence.

The probe to which the DNA of the invention hybridizes preferably consists of a sequence of at least 20 consecutive nucleotides, more preferably 40 nucleotides, even more preferably 50 nucleotides, and most preferably 100 nucleotides or more (up to 100%) of the coding sequence of the nucleotides listed in FIG. 2 (SEQ ID NO:1) or the complement thereof. Such a probe is useful for detecting expression of S2-6 in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from nucleotides 1 to 1029 of the nucleotides listed in FIG. 2 (SEQ ID NO:1), a region of FIG. 2 (SEQ ID NO:1) which includes at least one zinc binding LIM domain located between nucleotides 856 and 1011 [See amino acids in FIG. 3 and SEQ. ID. NO:3: S2-6 amino acid number 286 (CSGC . . . ) to 337 ( . . . CPTC)].

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence, e.g., a fusion protein. Also included is a recombinant DNA which includes a portion of the nucleotides listed in FIG. 2 (SEQ ID NO:1) which encodes an alternative splice variant of S2-6.

The DNA may have at least about 70% sequence identity to the coding sequence of the nucleotides listed in FIG. 2 (SEQ ID NO:1), preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The invention also includes a vector containing a DNA encoding a polypeptide which includes the amino acid sequence of FIG. 2 (SEQ ID NO:2), e.g., a construct in which the coding sequence is operably linked to a promoter or other regulatory sequences for expression of the polypeptide, and a cell containing such a vector. The cell may be procaryotic or eukaryotic and preferably expresses the recombinant polypeptide encoded by the nucleotides listed in FIG. 2 (SEQ ID NO:1).

A "vector" is defined as a replicable nucleic acid construct, e.g., a plasmid or viral nucleic acid. Vectors may be used to amplify and/or express nucleic acid encoding S2-6 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional/translational control signals. See for example, the techniques described in Sambrook et al., 1989, Molecular Cloning: A Laboratory Manual (2nd Edition), Cold Spring Harbor Press, N.Y., which are incorporated by reference. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

As stated above, the invention features a cell preferably expressing the recombinant polypeptide encoded by the nucleotides listed in FIG. 2 (SEQ ID NO: 1). This cell can be a prokaryotic cell, e.g., an *Escherichia coli* cell, or a eukaryotic cell. Eukaryotic cells that can be used in the invention include, but are not limited to, COS, CHO, HeLa, and Sf9 cells. In the case of a eukaryotic cell, the gene may or may not be integrated into the genome of the cell. Also included in the invention is an essentially homogeneous population of prokaryotic or eukaryotic cells, each of which contains (i.e., is transfected with) a recombinant S2-6 gene. Transfection can be transient or stable, and if desired can be carried out in vivo or ex vivo, using the patient's own cells.

The invention also includes a substantially pure DNA S2-6 protein (a) having a zinc binding LIM domain, (b)

whose mRNA is preferentially expressed in nonproliferating or growth inhibited human diploid fibroblasts, (c) whose mRNA is overexpressed in senescent human diploid fibroblasts or human diploid fibroblasts derived from a patient with Werner Syndrome, and (d) whose mRNA is not expressed in fetal human diploid fibroblasts, immortal cells or tumor derived cells. By zinc binding LIM domain is meant the presence of one to three repeats of a 52-residue segment containing two adjacent zinc binding domains separated by a two-residue linker $(CX_2CX_{17}HX_2C)$-$X_2$-$(CX_2CX_{17}CX_2C/H/D)$. The zinc binding LIM domain found in S2-6 is characterized by nucleotides 856 to 1011 of FIG. 2 (SEQ ID NO: 1) corresponding to amino acids 286 to 337 of FIG. 2 (SEQ. ID. NO:2 and SEQ ID NO: 3).

Preferably, the protein includes the amino acid sequence of SEQ ID NO:2 (human S2-6), e.g., in the form of a S2-6 fusion protein. By "protein" is meant any chain of amino acids, regardless of length or post-translational modification (e.g., glycosylation or phosphorylation). The amino acid sequence of the protein preferably differs from SEQ ID NO:2 solely by conservative amino acid substitutions, e.g., substitution of one amino acid for another of the same class (e.g., valine for alanine, arginine for lysine, etc.) or by one or more non-conservative substitutions, deletions, or insertions located at positions of the amino acid sequence where the changes do not destroy the function of the protein (e.g., binding to antibody specific to an epitope corresponding to the zinc binding LIM domain of S2-6). Preferably, the amino acid sequence of the zinc binding LIM domain protein S2-6 is at least 80%, more preferably 85%, more preferably 90%, and most preferably 95% identical to SEQ ID NO:3.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure S2-6 protein may be obtained, for example, by extraction from a natural source (e.g., old human diploid fibroblasts); by expression of a recombinant nucleic acid encoding an S2-6 polypeptide; or by chemically synthesizing the protein. Purity can be measured by any appropriate method, e.g., column chromatography such as immunoaffinity chromatography using an antibody specific for S2-6, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

Also included in this invention is substantially pure DNA that includes a sequence of at least 20 consecutive nucleotides of substantially pure DNA from the region of nucleotides 1 to 1029 of FIG. 2 (SEQ ID NO: 1). Also, this invention includes substantially pure DNA that includes a sequence of at least 20 consecutive nucleotides of substantially pure DNA encoding zinc binding LIM domain defined as nucleotides 856 to 1011 of FIG. 2 (SEQ ID NO: 3). The amino acid sequence of this zinc binding LIM domain is: CSGCDEIIFAEDYQRVEDLAWHRKHFVCEGCEQ LLSGRAYIVTKGQLLCPT C (See FIG. 3 (SEQ ID NO:3).

The chart below lists the different SEQ ID NOs that correspond to the nucleotides or amino acids and the figures in which these sequences appear.

| SEQ ID NO: | CORRESPONDS TO: | AS SHOWN IN FIGURE |
|---|---|---|
| 1 | Nucleotides 1–1549 | FIG. 2 |
| 2 | Amino Acids 1–343 | FIG. 2 |
| 3 | Zinc Binding LIM Domain: Nucleotides 856 to 1011 | FIG. 2 and FIG. 3 |

In addition to substantially full-length proteins, the invention also includes fragments (e.g., antigenic fragments) of the S2-6 proteins. As used herein, "fragment," as applied to a polypeptide, will ordinarily be at least 10 residues, more typically at least 20 residues, and preferably at least 30 (e.g., 50) residues in length, but less than the entire, intact sequence. Fragments of the S2-6 protein can be generated by methods known to those skilled in the art, e.g., by enzymatic digestion of naturally occurring or recombinant S2-6 protein, by recombinant DNA techniques using an expression vector that encodes a defined fragment of S2-6, or by chemical synthesis. The ability of a candidate fragment to exhibit a characteristic of S2-6 (e.g., binding to an antibody specific for S2-6) can be assessed by methods described herein. Purified S2-6 or antigenic fragments of S2-6 can be used to generate new antibodies or to test existing antibodies (e.g., as positive controls in a diagnostic assay) by employing standard protocols known to those skilled in the art. In one preferred embodiment, a monoclonal antibody is generated using the zinc binding LIM domain which corresponds to an amino acid sequence that is not homologous to the sequence of any other known proteins, to immunize an appropriate laboratory animal, such as a mouse. Also included in this invention are polyclonal antisera generated by using S2-6 or a fragment of S2-6 as the immunogen in, e.g., rabbits. Standard protocols for monoclonal and polyclonal antibody production known to those skilled in this art may be employed. The monoclonal antibodies generated by this procedure can be screened for the ability to identify recombinant S2-6 cDNA clones, and to distinguish them from known cDNA clones.

Also included in the invention are S2-6 proteins which are encoded at least in part by portions of SEQ ID NO:1, e.g., products of alternative mRNA splicing or alternative protein processing events, or in which a section of S2-6 sequence has been deleted. The fragment, or the intact S2-6 polypeptide, may be covalently linked to another polypeptide, e.g. which acts as a label, a ligand or a means to increase antigenicity.

The invention also includes a polyclonal or monoclonal antibody which specifically binds to S2-6. Preferably, this antibody specifically binds to an epitope in the zinc binding LIM domain of S2-6 which corresponds to the sequence shown is FIG. 3 (SEQ ID NO: 3). The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In preferred embodiments, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an ophthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting S2-6 DNA binding protein in a biological sample, which includes the steps of contacting the sample with the labelled antibody, e.g., radioactively tagged antibody specific for S2-6, and determining whether the antibody binds to a component of the sample. Antibody binding indicates that the sample contains a S2-6 polypeptide, and consequently, contains a zinc binding LIM domain.

As described herein, the invention provides a number of diagnostic advantages and uses. For example, the DNA binding protein S2-6 may be useful in diagnosing cancer in different tissues since this protein is absent in highly proliferating cells. Antibodies (or antigen-binding fragments thereof) which bind to an epitope specific for S2-6, e.g., the zinc binding LIM domain, are useful in a method of detecting S2-6 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labelled antibody (e.g., radioactively tagged antibody) specific for S2-6, and detecting the S2-6 protein using standard immunoassay techniques such as an ELISA. Antibody binding to the biological sample indicates that the sample contains a component which specifically binds to an epitope within S2-6, e.g., the zinc binding LIM domain. Lack of binding would be indicative of highly proliferating cells, e.g., cancerous cells.

Likewise, a standard Northern blot assay can be used to ascertain the relative amounts of S2-6 mRNA in a cell or tissue obtained from a patient suspected of having cancer, in accordance with conventional Northern hybridization techniques known to those persons of ordinary skill in the art. This Northern assay uses a hybridization probe, e.g. radio-labelled S2-6 cDNA, either containing the full-length, single stranded DNA having a sequence complementary to SEQ ID NO:1 (FIG. 2), or a fragment of that DNA sequence at least 20 (preferably at least 30, more preferably at least 50, and most preferably at least 100 consecutive nucleotides in length). Most preferably, the DNA hybridization probe would be complementary to a portion of FIG. 2 (SEQ ID NO:3) encoding the zinc binding LIM domain, particularly a part which is not homologous to any previously known DNA sequence. The DNA hybridization probe can be labelled by any of the many different methods known to those skilled in this art.

Antibodies to the S2-6 protein can be used immunohistochemically to identify the presence of S2-6 in normal tissues as compared to tissues suspected of having cancer wherein S2-6 binding would be absent. Also, antibodies to the S2-6 protein can be used in an immunoassay to detect reduced or absent levels of S2-6 protein expression in tissues suspected of neoplastic transformation. These same uses can be achieved with Northern blot assays and analyses.

As described herein, the invention provides a number of therapeutic advantages and uses. The data presented herein demonstrate that the S2-6 gene sequence may play role in regulation of DNA replication, cell growth and differentiation. Thus, as an anti-cancer therapeutic, causing the overexpression S2-6 mRNA in cancer cells could lead to inhibition of cell growth. This invention also includes a method of treating a patient suspected of having cancer whereby a patient suspected having cancer is identified, and then an effective amount of S2-6 protein is administered to the patient wherein such amount of S2-6 protein will inhibit DNA synthesis. Therapeutic uses of S2-6 protein can be based on the inhibition of cell division (DNA synthesis) through the overexpression of this protein by transfecting cells with a retroviral vector comprising and expressing the S2-6 gene. This will allow the constant overexpression of S2-6 mRNA and protein in target cells, e.g., neoplastic cells.

Also, increased S2-6 expression after exposure to a test compound can be used to screen a compound for its ability to reduce undesired cell division. Thus, this compound could be used as an anti-cancer therapeutic. This method includes the steps of obtaining a test compound, adding an effective amount of the test compound to a population of highly proliferating human cells for a sufficient amount of time, obtaining a control population of highly proliferating human cells, determining the amount of S2-6 expression in the cells exposed to the test compound and in the control cells, comparing the S2-6 expression between the cells exposed to the test compound and the control cells wherein an increase in S2-6 expression observed in the cells exposed to the test compound and not observed in the control cells is indicative of a compound capable of increasing S2-6 expression, wherein the increased S2-6 expression is an indication of a correlative reduction or elimination of undesired cell division. For this invention, highly proliferating human cells include, without limitation, fetal human diploid fibroblast cells, immortalized cells, and cancerous cells.

Also, decreased S2-6 expression after exposure to a test compound can be used to screen a compound for its ability to increase desired cell division. Thus, this compound could be useful for a variety of purposes where cell division and proliferation is desired, e.g., wound healing. This method includes the steps of obtaining a test compound, adding an effective amount of the test compound to a population of senescent human diploid fibroblast cells for a sufficient amount of time, obtaining a control population of senescent human diploid fibroblast cells, determining the amount of S2-6 expression in the cells exposed to the test compound and in the control cells, comparing the S2-6 expression between the cells exposed to the test compound and the control cells wherein a decrease in S2-6 expression observed in the cells exposed to the test compound and not observed in the control cells is indicative of a compound capable of decreasing S2-6 expression, wherein the decreased S2-6 expression is an indication of a correlative increase in cell division. For this invention, senescent human diploid fibroblast cells include, without limitation, human diploid fibroblasts derived from a patient with Werner Syndrome.

For administration to human patients, antibodies specific for S2-6 can be humanized by methods known in the art, e.g, by a commercial service (Scotgene, Scotland; Oxford Molecular, Palo Alto, Calif.). Monoclonal antibodies can be purified using known methods, such as absorption onto immobilized Protein A or immunoaffinity chromatography. Following purification, the MAbs of the invention or immunologically active fragments thereof, e.g., Fab, (Fab)$_2$, or Fv, can be administered to patients in a pharmaceutically acceptable excipient such as physiological saline. The MAbs and/or antibody-based compounds of the invention, e.g., MAbs linked to therapeutic agents, can be administered by any standard route including intraperitoneally, intramuscularly, subcutaneously, intravenously or intra-arterially. It is expected that the preferred route of administration will be intravenous or intra-arterial. These compounds can be administered systemically to the bloodstream as well as locally within the blood vessel at the site of clot formation.

As is well known in the medical arts, the dosage for any one patient will depend on many factors, including the patient's general health, extent of disease, sex, size, body surface area, and age, as well as the particular compound to be administered, time and route of administration, and other drugs being administered concurrently. Dosages for compounds of the invention will vary, but a preferred dosage for intravenous administration is approximately 1 $\mu$g to 500 $\mu$g/ml blood volume. Determination of correct dosage for a given application is well within the abilities of one of ordinary skill in the art of pharmacology.

The therapeutic agents described herein may be linked to an antibody specific for S2-6 using a covalent bond, such as a disulfide bond or a covalent crosslinking agent, by employing standard protocols well known in the art.

For this invention, HDF means human diploid fibroblast cells. By yHDF is meant young HDF. By sHDF is meant senescent HDF. By oHDF is meant old HDF. For this invention, old HDF or oHDF and sHDF are used interchangeably. By MPD$_{max}$ is meant the maximum number of Mean Population Doublings accruing until phaseout.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 2A, 2B, and 2C shows the nucleotide and deduced amino acid sequence of the largest insert obtained for S2-6 (1549 nucleotides). The nucleotides and amino acids are numbered in relation to the first nucleotide of the clone.

Werner syndrome skin fibroblasts. PolyA$^+$RNA equality of loading and evenness of transfer to ZETA Probe nylon membrane were assessed by control hybridization with $^{32}$P end-labeled oligo-dT probe.

Figure 5A:
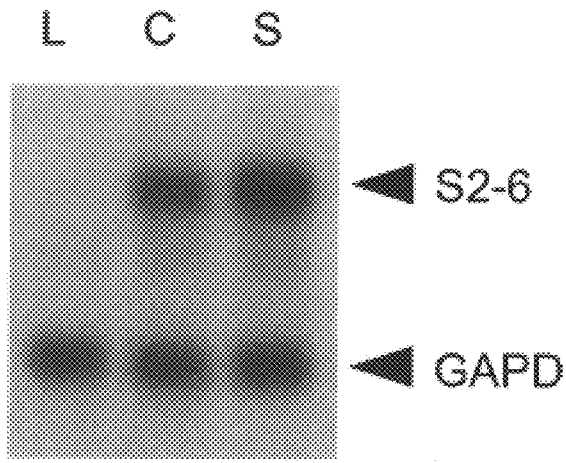

FIG. 5A is a photograph of a Northern gel of S2-6 mRNA expression under different growth conditions. Normal skin fibroblasts (A2 skin HDF at MPD26 (MPDmax=56) logarithmically growing (L) in the presence of 15% fetal bovine serum (FBS) were made quiescent by contact inhibition after growing in the presence of 15% FBS for 6 days (C) or by serum depletion for 2 days (S). Poly (A$^+$) RNA was isolated and 2 _g of polyA$^+$RNA were loaded on each lane. For equal loading and evenness of transfer the same filter was hybridized with GAPD (glyceraldehyde-3-phosphate dehydrogenase).

Figure 5B:
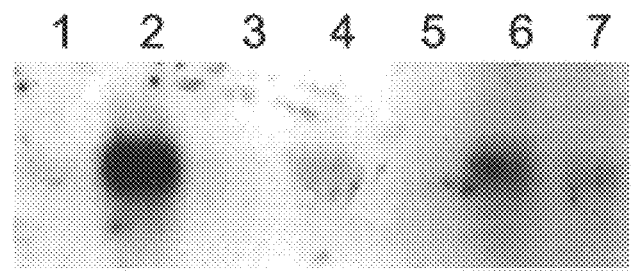

FIG. 5B is a photograph of a Northern gel of S2-6 mRNA expression in transformed cell lines. Lanes 1 and 2 contained 2 $\mu$g of poly(A$^+$)RNA derived from proliferating and confluent A2 HDF, respectively. Lanes 3–7 contained 10 $\mu$g of poly(A$^+$)RNA derived from the following cell lines: (3) MRC5 fetal lung HDF transformed by SV40; (4) HTB140 melanoma metastatic to lymph node; (5) HTB40, adenocarcinoma, small intestine; (6) 293, kidney cells transformed by adenovirus; (7) CaCl, myeloma, bone marrow.

Figure 6A:
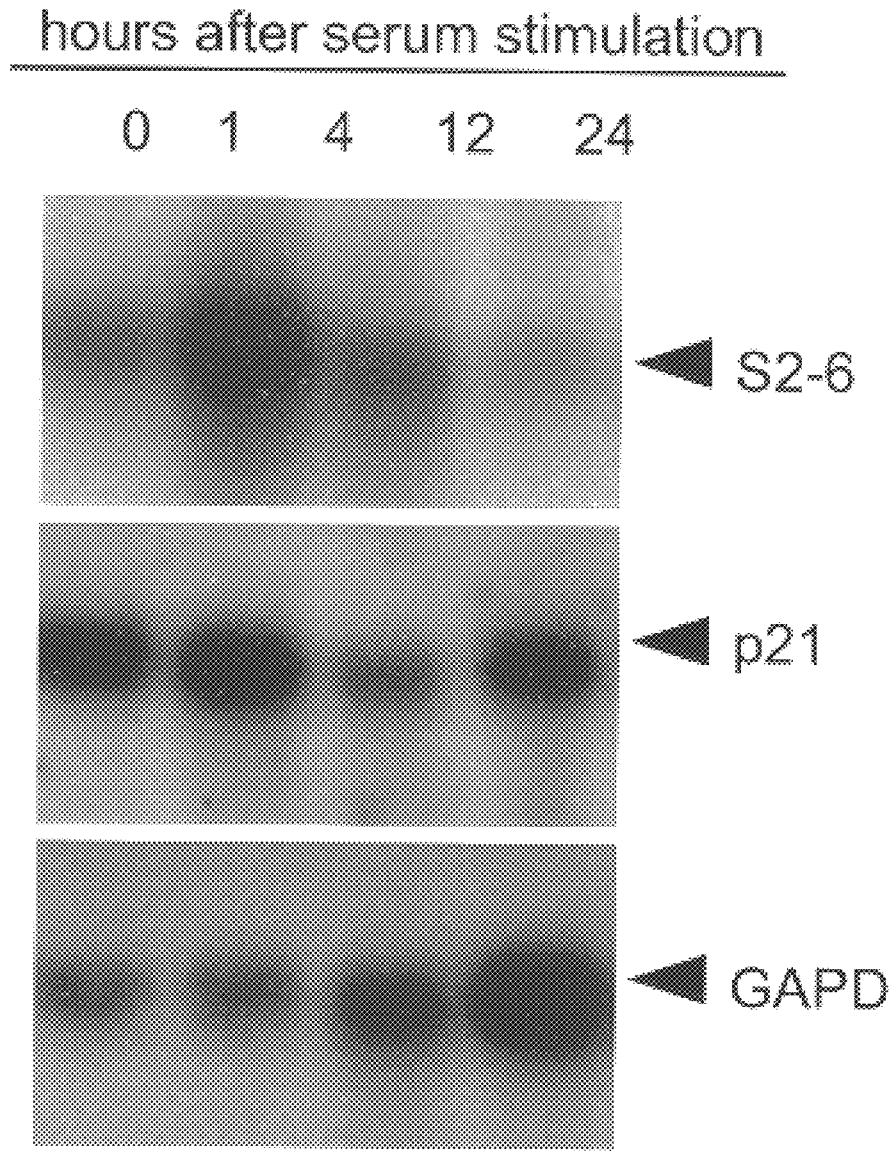

FIG. 6A shows a Northern blot analysis of S2-6, p21 and GAPDH expression at different time points after refeeding quiescent fibroblasts. Each lane contained 1 $\mu$g of poly(A$^+$) RNA. FIG. 6B shows a graphic representation of S2-6 mRNA expression and DNA synthesis at the same time points after refeeding.

FIG. 7 is a schematic representation showing an alignment of several "zinc finger" sequences: S2-6 "zinc finger," part of LIM domain; three zinc finger domains from clone S1-3; *D. melanogaster* hunchback protein; mkr3, murine Kruppel-like protein; and cKrl, chicken Kruppel-like protein. The bottom line represents the sequence for the S2-6 "zinc finger", part of LIM domain. Amino acids involved in zinc binding are boxed by solid lines; highly conserved amino acids are boxed by dotted lines.

DETAILED DESCRIPTION OF THE INVENTION

The construction and screening of a senescent cDNA library provided an initial approach toward determining the identities of genes which may be causally involved in the senescence of HDF. In electing to doubly subtract, it was intended that this strategy would substantially increase the probability of revealing relatively non-abundant RNA transcripts of gene sequences that may play a regulatory role. The majority of cDNA clones isolated from the subtracted library are expressed at a very low level. With this double substraction technique, clones which may play a role in regulation of gene expression can be identified and further studied. The rationale for using cultured WS cells as model cells is evident from the description on WS provided above.

Identification/Characterization of a Gene Overexpressed in Senescent Cells

To uncover transcripts of very low abundance coding for proteins with a possible regulatory function, a second, subtracted WS cDNA library (W8) was constructed in the λZAPII phage system (Stratagene). This system enabled gene inserts to be converted into single-stranded antisense cDNAs complementary to polyA$^+$RNA, which facilitates subsequent subtractive enrichment of senescence-specific cDNAs. Two sequential steps of subtraction were performed on this cDNA library: (1) to deplete cDNAs corresponding to mRNAs common to young and senescent cells, e.g., housekeeping gene transcripts, and then (2) to deplete cDNAs that represented relatively abundant mRNAs, predominantly encoding proteins secreted into the extracellular matrix (ECM) and ECM-associated proteins, which had been identified as overexpressed in the first WS cDNA library.

Cell Culture

Table 1 shows a variety of human diploid fibroblast cell lines available for use. Postnatal strains were derived from forearm skin biopsies. Skin fibroblast cultures from WS8 and WS12, two unrelated patients with classical Werner syndrome, were a gift from Dr. S. Murano, Chiba University (Chiba, Japan). HSC172 cells were derived from fetal lung fibroblasts. Cells were cultivated in regular growth medium (RGM) consisting of Eagle's minimum essential medium (MEM) supplemented with a 15% fetal bovine serum (FBS). Young HDF were defined as proliferatively competent cells in the first half of their replicative lifespan, while old HDF were cells with attenuated proliferative capacity in the last 10% of their replicative life span.

TABLE 1

STRAINS OF HUMAN DIPLOID FIBROBLASTS USED

| Cell Strain | Age Gender | Cell Type | Maximum Mean Populations Doublings |
|---|---|---|---|
| NORMAL | | | |
| HSC172 | fetal F | lung | 62 |
| A25 | 9 F | skin | 48 |
| A2 | 11 M | skin | 54 |
| A23 | 23 M | skin | 56 |
| A8 | 31 M | skin | 56 |
| J065 | 56 M | skin | 44 |
| A33 | 70 M | skin | 35 |
| A35 | 76 M | skin | 33 |
| J088 | 76 F | skin | 44 |
| WERNER SYNDROME | | | |
| WS12 | 46 M | skin | 19 |
| WS8 | 48 M | skin | 18 |

RNA Isolation

PolyA$^+$RNA was isolated by Fast-Track kit (Invitrogen). Total RNA was isolated according to the acid guanidinium thiocyanate-phenol-chloroform method (Chomczynski and Sacchi, 1997). For Northern analysis, total and polyA$^+$ RNAs were resolved on 1% agarose formaldehyde gels and transferred to ZETA Probe nylon membranes. RNA integrity, equality of loading, and evenness of transfer were assessed by control hybridizations to glyceraldehyde-3-phosphate dehydrogenase (GAPD) or β-actin cDNAs. All hybridizations were performed under high stringency conditions (Church and Gilbert, 1984).

Construction of W8 cDNA Library

A WS cDNA library was constructed as previously described (Lecka-Czernik et al., 1995). Briefly, 5 µg of polyA$^+$RNA isolated from WS8 cells six days after subculture in RGM was used as a template. The W8 cDNA library was constructed in the λZAPII system (Stratagene), which allows for unidirectional cloning, easy conversion of phage to plasmid form, and rescue as a single-stranded cDNA complementary to its mRNA as a Bluescript phagemid. The complexity and quality of the library were checked by screening with a cDNA corresponding to the 3' untranslated region (UTR) of β-actin cDNA (Ponte et al., 1984). The W8 cDNA library, before amplification, consisted of $2.6 \times 10^5$ independent cDNA clones.

Biotinylation

PolyA$^+$RNA was biotinylated using Photoprobe-Biotin (Vector Laboratories), a photoactivatable form of biotin (PAB). Ten micrograms of polyA$^+$RNA were resuspended in 10 µL of 0.1 mM EDTA, pH 8.0, mixed with an equal volume of Photoprobe-Biotin stock solution (1 µg/µL) and irradiated for 15 min in an ice bath, 10 cm below a sunlamp (wave length 350–370 nm). Following labeling sample volume was increased to 100 µL by the addition of 0.1M Tris-HCl, pH 9.5, and unreacted PAB was removed by repeated extraction with an equal volume of 2-butanol. RNA was subjected to a second biotinylation reaction, followed by 2-butanol extractions and [PAB]RNA ethanol precipitation.

Subtraction

Single-stranded (ss)DNA representing Bluescript phagemid containing cDNA inserts was rescued from the λZAPII W8 library using R408 helper phage according to Schweinfest et al. (1990). Subtractive hybridization was carried out according to Schweinfest et al. (1990), Duguid et al. (1988), and Sive and St. John (1988), with modifications. [PAB]RNA (10 µg) from cell strain HSC172 representing normal fetal HDF was co-precipitated with 1 µg of ssDNA, 1 µg poly(A) and 1 µg poly(C) in the presence of glycogen. The precipitate was dissolved in 5 µL of HE (10 mM Hepes, pH 7.5, 1 mM EDTA) and 5 µL of 2×HB (1×0.5M NaCl. 50 mM Hepes, pH 7.6, 2 mM EDTA, 0.2% SDS). The hybridization mixture was overlaid with mineral oil, heated at 95° C. for two minutes, and incubated at 65° C. for 45 h to achieve R$_o$t ~3000, necessary for promotion of hybridization between rare RNA sequences. To remove ssDNA-[PAB] RNA hybrids and unhybridized [PAB]RNA, hybridization mixture was diluted 10-fold with HB-SDS (without SDS) and 10 mg of avidin D covalently linked to VECTREX matrix (Vector) was added. The mixture was then incubated at 60° C. for 30 min with rotary agitation and centrifuged for 30 s at 3000×g. The supernatant was collected. Resins were washed three times with 100 µL HB-SDS, and combined supernatants were incubated again with 10 mg of VECTREX-Avidin D followed by consecutive washing as above. Collected supernatant was combined, extracted once with phenol:chloroform, once with chloroform, and ethanol precipitated. To rescue ssDNA from the complex with [PAB]RNA, VECTREX-Avidin D resins used for subtraction were incubated for 15 min at 95° C. in the presence of 200 μL HB-SDS, cooled on ice, centrifuged, extracted with phenol:chloroform and chloroform, and precipitated as above. The efficiency of subtraction was examined by dot-blot hybridization of β-actin cDNA probed with [$^{32}$P]-labeled ssDNA present in the collected supernatants. The level of signal achieved was compared using as a probe either DNA remaining as unhybridized fragments or DNA rescued from [PAB]RNA-DNA hybrids. A 100-fold reduction in signal was seen in blots hybridized to the remaining ssDNA, which indicated a high level of subtraction. The second round of subtraction was performed with in vitro transcribed RNAs (Krieg and Melton, 1984) representing clones previously identified as abundantly expressed in WS cells. RNAs were mixed in a ratio representing their abundance in the W8 cDNA library before subtraction and procedures were performed under the identical conditions as in the first round.

Transformation

The subtracted ssDNA was converted to double-stranded DNA prior to transformation into XL1Blue *E. coli*. Synthesis of the second DNA strand was performed using SK primer according to Schweinfest et al. (1990). Clones with cDNA insert were identified by color selection of colonies in the presence of X-Gal and IPTG. Isolated cDNA clones represented the subtracted W8 library referred to as sW8.

Differential Screening of sW8 Library

Differential (±) screening was performed with five replicate dot-blots containing 5 μg of immobilized plasmid DNA representing each cDNA clone from the sW8 library (Maniatis et al, 1989). Each blot was probed separately with a [$^{32}$P]-labeled cDNA derived from polyA$^+$RNA of different cell strains. Probes with high specific activity were achieved as follows. Annealing reaction was performed using 0.4 μg polyA$^+$RNA and 0.8 μg of random decamers. The mixture was heated at 70° C. for 10 min and chilled on ice. cDNA synthesis was performed using Superscript II Reverse Transcriptase (Gibco BRL). A typical reaction consisted of: 7 μL annealed polyA$^+$RNA with decamers, 4 μL 5× first strand buffer (Superscript II), 2 μL 0.1M DTT, 1 μL dNTPs (10 mM of each except dCTP) and 5 μL [α-$^{32}$P]dCTP (spec. activity 3000 ci/mM). The mixture was warmed for two minutes at 37° C., 1 μL (200 U) Superscript II Reverse Transcriptase was added, and incubation continued for one hour at 37° C. Remaining template RNA was digested by 1 μL (1.5 U) RNaseH for 30 min at 37° C. and probes were purified on G-25 Sepharose spin-columns. The efficiency of labeling was ~7.5×10$^7$ CPM/μg RNA. Hybridization was carried out under high stringency conditions using the same amount of specific radioactivity for each cDNA probe.

DNA Sequencing

DNA sequencing of double-stranded insert cDNA was performed with Sequenase (U.S. Biochemical) and synthetic oligonucleotide primers in the chain termination method (Sanger et al., 1977). A search of the GenBank/EMBL databases was conducted for sequence homology and analysis was performed with the Wisconsin Genetics Computer Group software package.

Deposit

Under the terms of the Budapest Treaty on the International Recognition of the Deposit of Microorganisms for the Purpose of Patent Procedure, a plasmid containing human S2-6 (S2-6 clone in the pBluscript SK™ vector [Stratagene]) was deposited with the American Type Culture Collection (ATCC) of Rockville, Md., USA, on Jun. 28, 1996, and was given ATCC designation number 97642. Applicant's assignee, Board of Trustees of the University of Arkansas, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

Construction and Screening Of an Unsubtracted sW8 cDNA Library

This library was constructed for the purpose of isolating genes that are specifically expressed or overexpressed during aging. A Werner syndrome (WS) cDNA library was first constructed in the Okayama-Berg eukaryotic expression vector. Differential screening of this library revealed eighteen distinct cDNAs whose cognate RNA transcripts were abundantly overexpressed in WS and normal sHDF, compared to yHDF (Murano, et al. 1991). Among the 18 cDNAs, nine clones encoded known proteins including α1(I) procollagen, α2(I) procollagen, fibronectin (FN), ferritin heavy chain, osteonectin (or SPARC), IGF binding protein-3 (IGFBP-3), thrombospondin, αB-crystallin and plasminogen activator inhibitor-1 (PAI-1). Some of them (e.g. IGFBP-3, SPARC, PAI-1 and FN) can inhibit DNA synthesis by modulating extracellular signals (Symington 1992; Grigoriev, et al. 1994). Overproduction of FN and PAI-1 can interfere with normal regulation of blood clotting and predispose to atherogenesis (Rasoamanantena, et al. 1994; Goldstein, et al. 1994). Excessive accumulations of SPARC and thrombospondin, by virtue of their Ca$^{2+}$-binding properties, could predispose to osteopenia and the tendency to develop osteoporosis (Thweatt, et al. 1993; Termin 1990).

Among the nine previously unknown clones, WS3-10 cDNA codes for a cystolic smooth muscle protein that putatively binds intracellular Ca$^{2+}$ and whose forced expression leads to suppression of Ca$^{2+}$-mediated membrane currents, similar to the suppressed currents that arise spontaneously in sHDF (Thweatt, et al. 1992; Liu, et al. 1994). The remaining seven clones contain the highly repetitive family of Alu elements, whose functional significance is unknown, but when introduced into HeLa cells appear to have an inhibitory effect on DNA synthesis (Sakamoto, et al. 1991). It is noteworthy, that all of the cDNA clones isolated as overexpressed in WS HDF are also overexpressed in normal sHDF. Once normal HDFs become senescent, they appear to generate the same downstream changes in genetic expression as prematurely senescent WS HDF. This bolsters the argument that a causal connection exists between senescence of HDF in vitro and biological aging in vivo.

Construction and Differential Screening of a Subtracted sW8 cDNA Library

To uncover transcripts of very low abundance coding for protein with a possible regulatory function, a second, subtracted WS cDNA library (W8) was constructed in the λZAPII phage system (Stratagene). This enabled the gene inserts to be converted into single-stranded antisense cDNAs complementary to polyA$^+$RNA, which facilitates efficiency of subsequent annealing and subtraction. Below two sequential steps of subtraction were performed on this cDNA library (see outline of scheme below): Step (1) to deplete cDNAs corresponding to mRNAs common to young and senescent cells such as housekeeping gene transcripts; and then Step (2) to deplete cDNAs that represented relatively abundant mRNAs, predominantly encoding proteins secreted into the extracellular matrix (ECM) and ECM-associated proteins, which had been identified earlier in the first WS cDNA library.

In total, these two steps served to deplete cDNAs that represented mRNAs common to young and senescent cells, such as housekeeping gene transcripts, and sequences representing relatively abundant mRNAs, predominantly encoding secreted proteins that had been identified earlier as overexpressed in the first WS cDNA library (Murano et al., 1991).

In the second step, the remaining cDNAs were subtracted with biotinylated mRNAs transcribed in vitro from cDNA clones for FN, ferritin heavy chain, α1(I) procollagen, α2(I) procollagen and IGFBP-3, all of which were found to be overexpressed in the first WS library (Murano, et al. 1991). After subtraction, antisense single-stranded DNAs were converted to double-stranded DNA using the Klenow fragment of E. coli polymerase I, and this DNA was transfected into XL1Blue E. coli cells. This enabled the transformants to be screened for their possession of cDNA inserts in the presence of IPTG and X-gal, as inducer and indicator of β-galactosidase expression, respectively (Lecka-Czernik, et al. 1995).

Differential Screening of the Subtracted WS cDNA Library

Figure 1:
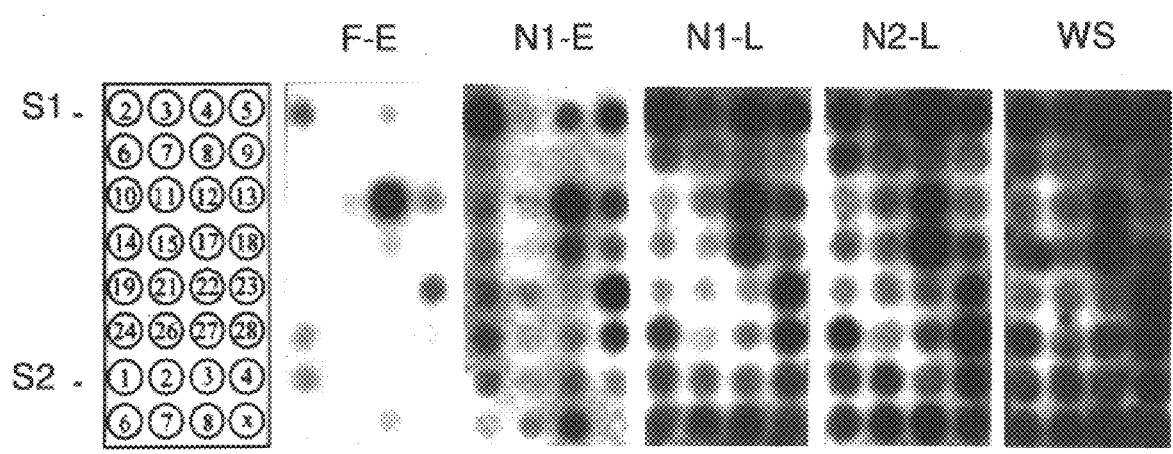
FIG. 1 is a photograph of dot-blots representing mRNA expression of clones, dependent on the cell type, derived from a subtracted WS fibroblast cDNA library.

After these two subtraction steps, 31 different clones were obtained differentially screened on five replicate dot blots (FIG. 1). FIG. 1 is a photograph of an immunoblot repre-

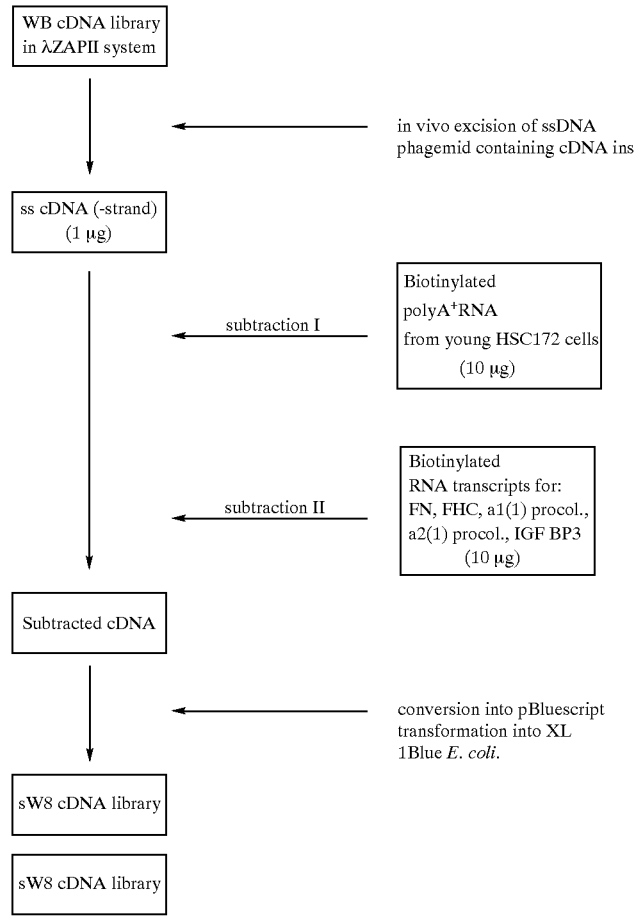

First, antisense cDNAs were subtracted with biotinylated polyA+RNAs obtained from vigorously growing, normal fetal fibroblasts (HSC172) followed by removal of duplexes and unannealed single-stranded RNA by avidin binding. Hybridization was done under high stringency conditions with a 10 fold excess of biotinylated polyA+RNA. Hybrids between biotinylated mRNA and cDNA and unannealed mRNA were removed by avidin binding and phenol extraction (Schweinfest, et al. 1990).

senting a subtracted WS fibroblast cDNA library. $^{32}$P-labeled cDNAs derived from the following polyA+RNAs were used as probes: (1) early-passage, vigorously growing fetal HDF; (2) early passage, postfetal normal HDF; (3) the same strain of normal postfetal cells nearing the end of their replicative lifespan ("old" or senescent HDF); (4) a second strain of normal postfetal late-passage HDF; and (5) prematurely senescent WS HDF. Five µg of plasmid DNA containing 31 specific cDNA inserts from the subtracted library identified in two stages (S1 and S2) and one cDNA from the previous unsubtracted library (ref. 41) for comparative purposes (WS19-9 indicated by x) were loaded on five replicate filters. Probes were prepared using 1 μg of polyA⁺RNA derived from several cell types, primer extension by reverse transcriptase, dNTPs and 50 μCi[a-$^{32}$P]dCTP, followed by digestion of the remaining RNA with 1.5 U RNaseH and purification of probes on G-50 Columns. Hybridization was carried out at high stringency using $1 \times 10^7$ CPM/ml of each probe. Left panel, scheme depicting replicate dot blot arrays probed with $^{32}$P-cDNA derived from: F-E, normal early-passage fetal fibroblasts (strain HSC172)MPD level 9 ($MPD_{max}$=62); N1-E, normal early passage A2 skin fibroblasts at MPD 23 (11 year old donor, $MPD_{max}$=54); N1-L, A2 fibroblasts at late passage (MPD 51); N2-L, normal late-passage A25 skin fibroblasts at MPD (9 year old donor, $MPD_{max}$ 48); WS8 skin fibroblasts from a 46 year old WS subject at MPD 12 ($MPD_{max}$=18) (ref. 44). As a result of this probing, the 31 clones were classified into four groups according to their levels of RNA expression. Clone S2-6, which is the subject of the instant invention, falls into Group I.

Group I: Clones not expressed in fetal HDF, but overexpressed in Old HDF and WS HDF.

This group contains 9 distinct clones; one known (S1-9) and eight novel showing no homologies to known proteins. See Table 2 below. S1-9 encodes the enzyme acid sphingomyelinase whose mRNA accumulates in HDF in direct proportion to donor age. This enzyme is of interest since its catalytic cleavage of sphingomyelin generates ceramide, whose elevated level is implicated in senescence of HDF by its ability to promote growth arrest and repression of AP-1 transcription factor activity (Obeid 1994). Other well documented studies have shown that ceramide can trigger signal transduction pathways leading to activation of NFκB and the MAP kinase phosphorylation cascade, processes which can induce cell apoptosis in some experimental systems (Obeid, et al. 1993; Jarvis, et al. 1994; reviewed in Kolesnick, et al. 1994). S1-5 encodes a member of the EGF-like protein family with an EGF-like domain consensus sequence highly homologous to those present in several known extracellular proteins which play a role in cell growth, development and cell signaling, such as TGF-β1 binding protein (Kanzaki, et al. 1990), Notch multifunctional receptor (Wharton, et al. 1985) and nidogen (Mann, et al. 1989). S1-5 mRNA is overexpressed in normal sHDF and WS HDF, is induced by growth arrest in young normal cells, but is significantly decreased by high concentrations of serum, conditions which promote cellular proliferation (Lecka-Czernik, et al. 1995). Paradoxically, microinjection of S1-5 mRNA into yHDF stimulated DNA synthesis by an apparent autocrine/paracrine mechanism. Thus the S1-5 gene product may represent a negative and/or positive factor whose ultimate activity is modulated by the cell environment, a similarity it shares with other members of the EGF-like protein family. S1-3 encodes a hitherto unknown protein that contains three "zinc finger" domains, suggesting that it is a DNA binding protein (Klug, et al. 1987). S2-6, the subject of this invention encodes a new member of the LIM protein family (Sanchez-Garcia, et al. 1994). Lastly, S1-15 shows a 70% similarity to human α2-chimerin (Hall, et al. 1993). The remaining 3 clones have no significant homology to known proteins.

TABLE 2

GROUP I CLONES mRNA OVEREXPRESSED IN OLD AND WS HDF AND NOT EXPRESSED IN FETAL CELLS

| cDNA CLONE | Levels of RNA Expression | | | | | mRNA (kb) | cDNA Sequenced (kb) | Identity/ Similarity | References |
|---|---|---|---|---|---|---|---|---|---|
| | F-E | N1-E | N1-L | N2-L | WS | | | | |
| S1-3 | − | + | ++ | ++ | ++ | 2.8; 1.8 | 1.2 | "Zinc Finger" protein | Klug and Rhodes, 1987 |
| S1-5 | − | ++ | +++ | +++ | +++ | 3.0; 2.2 | 3.0 | EGF-Like Family | Lecka-Czernik et al., 1995 |
| S1-7 | − | − | + | + | + | smear | 0.2 | None | |
| S1-8 | − | − | + | + | + | 5.4; 2.3; 1.3 | 0.2 | None | |
| S1-9 | + | + | ++ | ++ | ++ | 2.7 | 0.5 | Acid sphingomyelinase | Schuchman et al., 1991 |
| S1-15 | − | + | ++ | ++ | +++ | 2.3; 1.9 | 0.2 | 2-chimerin | Hall et al., |
| S1-28 | − | ++ | +++ | +++ | +++ | >20 | 0.2 | None | |
| S2-2 | − | + | ++ | ++ | ++ | 2.0 | 0.5 | None | |
| S2-6 | − | + | ++ | +++ | +++ | 2.0 | 1.5 | LIM Family | Sadler et al., 1992 |

Group II: Clones expressed in fetal HDF and yHDF, but overexpressed in sHDF and WS HDF.

This group consists of 6 clones, five of which encode known proteins including fibronectin (FN) (Kornblihtt, et al. 1983), osteonectin (SPARC) (Swaroop, et al. 1988), two translation factors: eukaryotic initiation factor-2β (eIF-2β) (Pathak, et al. 1988) and elongation factor-1α (EF-1α) (Uetsuki, et al. 1989) and protein associated with low tumor metastatic potential nm23 (Steeg, et al. 1988). FN and SPARC were previously isolated as overexpressed clones from the unsubtracted WS cDNA library (Murano, et al. 1991). Therefore it is evident, that not all FN gene sequences were removed completely by this subtraction procedure. The S1-4 cDNA clone shows no identity or homology to known sequences.

Group III: Clones not expressed in fetal HDF but expressed in yHDF, sHDF and WS HDF.

This group contains 12 clones which are specific for postnatal HDF. Four of them: S1-18, S1-19, S1-21 and S2-4, represent the gene sequence for human pregnancy-specific β-1 glycoprotein known also as carcinoembryonic antigen SG5 (Rooney, et al. 1988). S1-14 has a 91% similarity but only 36% identity to human glutaminyl-tRNA synthetase (Fett, et al. 1991) and S2-3 has a 90% similarity and 69% identity to glycyl-tRNA synthetase from Bombyx mori (Nada, et al. 1993).

Group IV: Clones expressed at a similar level in all four cell types

This group contains 3 clones, indicating incomplete subtraction. Thus, the strategy to construct and screen a subtracted senescent cDNA library provided an approach to identity genes causally involved in the senescence of HDF. The subtractive strategy, in contradistinction to the nonsubtractive procedure applied in the first library, would more likely reveal relatively nonabundant gene sequences that play a regulatory role in cell proliferation. Because even ostensibly young cultures contain an admixture of senescent cells, housekeeping gene transcripts, common for young and old cells, were subtracted out using mRNA from normal, fetal lung fibroblasts (Harley and Goldstein, 1978). This resulted in isolation of 12 clones that seemed to be specific for skin, in contrast to lung fibroblasts and were equally expressed in young and old skin fibroblasts.

Despite this, from the subtraction protocol, among the 31 isolated clones, 15 of them were overexpressed in senescent and WS HDF, compared to early passage HDF, e.g., S2-6 which is the subject of the instant invention. In contrast to the first unsubtracted WS cDNA library, the sW8 library consisted mainly of clones representing transcripts of very low abundance for both nuclear and cytoplasmic proteins, e.g., S2-6, the subject of this invention. As will be demonstrated below, S2-6 contains zinc finger "LIM" domains which may play an important regulatory role in cell proliferation and DNA synthesis.

Characterization of Clone S2-6 Overexpressed in Senescent and WS HDF

The following studies were performed on S2-6 to more fully understand the structure and function of clone S2-6.

S2-6 DNA Sequence Analysis

The analysis of clones isolated from a subtracted WS cDNA library led to the identification of a novel cDNA, S2-6 that codes for a zinc binding LIM protein. The originally isolated S2-6 clone was sequenced and shown to contain a 1.5 kb cDNA insert (See FIGS. 2A, 2B, and 2C). FIGS. 2A, 2B and 2C show the nucleotide and deduced amino acid sequence of the largest insert obtained for S2-6. The nucleotides are numbered in relation to the first nucleotide of the clone. As is evident, S2-6 insert is 1549 nucleotides in length and encodes for 343 amino acids (nucleotides 1 through 1029 of SEQ ID NO: 1). Also, approximately 600 nucleotides are missing from the 5' end.

This cDNA insert was sequenced and analysis of the entire original clone revealed a 343 amino acid putative protein with a "zinc binding LIM" domain. From this data, it was established that clone S2-6 represents a new member of the zinc binding LIM protein family. Due to the very low abundance of S2-6 cognate transcripts, which is also reflected by the low abundance of these cDNA clones in the library, it was found that conventional screening of the cDNA library would be ineffective and laborious in attempting to obtain the full length cDNA for S2-6. Therefore, PCR analysis of the λZAP II unsubtracted cDNA library was performed to isolate the missing fragments representing the 5' end of the S2-6. This procedure was successfully used in isolating the full-length, very low frequency, c-myb cDNA clone (Amaravadi, et al. 1990). Briefly, subpools of λZAP II library were screened in phage form using PCR amplification, with one primer (right) specific for the 5' end of the cDNA and the second (left) non-specific primer corresponding to a vector sequence. Positive pools were detected by Southern analysis of PCR products followed by dilution and screening again by the same method until single clones were isolated. As opposed to conventional methods, this method allows screening of a larger number of clones and simultaneously identifies pools that contain clones with the longest cDNA inserts.

Primers specific for the analyzed clones and the corresponding vector primers were designed. To avoid nonspecific PCR amplification, each pair of primers had the same melting temperature ($T_m$), length and GC content, and no homologies on their 3' ends to other known sequences as established by searching Genbank/EMBL databases. First, $1.5 \times 10^6$ clones which were divided into 30 subpools containing 50,000 pfu (plaque forming units) were screened. PCR amplification of each subpool was followed by DNA agarose gel electrophoresis and Southern analysis. Positive pools containing the PCR product of appropriate length were diluted to 10 subpools of 500 pfu each, and the amplification reaction was performed again followed by Southern analysis. Positive pools were plated at 100 pfu/plate and screened by the conventional method of plaque hybridization. For isolating the full length S2-6 clone, the above strategy was followed which included screening cDNA library subpools by PCR analysis. Subpool clones with PCR generated fragments approximately 500 nucleotides in size were studied. Two such subpools were identified and isolating separate clones and performing DNA sequencing analysis is currently underway.

Amino Acid Alignment of LIM Sequences of S2-6 Protein. Murine Testin and Hic-5

Figures 3, 4:
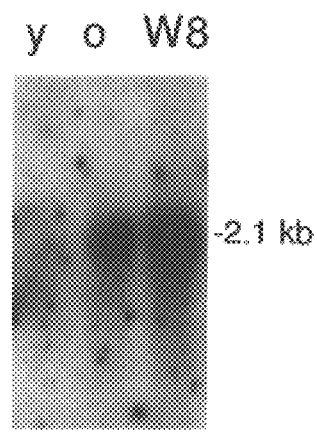
FIG. 3 is a schematic diagram showing the alignment of LIM sequences for S2-6 protein, murine testin, and Hic-5. *Amino Acids in Solid Boxes* - Amino acids which play a role in zinc binding, e.g., "zinc finger" domains; *Amino Acids Marked by Dots* - The position of other highly conserved amino acids is marked by solid dots.
FIG. 4 is a photograph of a Northern gel showing S2-6 mRNA expression. Each lane contained 3 $\mu$g of polyA$^+$ RNA. "y": young, early passage fibroblast cells; "o": old, late passage human skin fibroblasts; "W8"

DNA sequencing analysis of the 1.5 kb cDNA insert, using GenBank/EMBL databases, revealed that it contained on its C-terminus one LIM domain and had significant homology over the entire cDNA fragment at the DNA level (61.8% identity) and at the protein level (58.4% identity and 88.8% similarity) to a murine protein named "testin", whose sequence (submitted to GenBank database in June 94), as yet, has not been published in a professional journal (See FIG. 3).

FIG. 3 is a schematic diagram showing the alignment of LIM sequences for S2-6 protein, and other LIM family members, murine testin, and Hic-5. *Amino Acids in Solid Lined Boxes* - Amino acids which play a role in zinc binding, e.g., "zinc finger" domains are shown in solid lined boxes; *Amino Acids Marked by Dots* - The position of other highly conserved amino acids is marked by solid dots. Murine testin, a protein consisting of 423 aa, contains two LIM domains on its C-terminus. Another protein to which the S2-6 LIM domain shows very high homology is hic-5 (46), a protein shown to have a role in cell growth inhibition. From these data, S2-6 protein belongs to the LIM-only protein family, whose members have a role in regulation of transcription and cell proliferation.

Assessment of S2-6 protein DNA Binding Properties

The S2-6 putative protein contains one LIM domain which consists of two types of "zinc fingers": $C_2H_2$ and $C_2C_2$. DNA sequence analysis using the GenBank Database for transcription factors revealed that this protein contains no homeodomain determined to be a DNA binding domain, however the region between amino acids 170–200 does show significant homologies to known transcription factors. Because of the present controversy about the DNA binding ability of LIM domains, the presence of $C_2H_2$ zinc binding domain highly homologous to those present in transcription factors, and homologies in the region outside the LIM domain to protein sequences of known transcription factors like the H15 homeobox-containing gene from the honeybee and E2 from human papillomavirus (92,93). Studies are performed to determine whether this protein can specifically bind to DNA and the protein region responsible for this binding is also identified.

A synthetic random oligonucleotide library is used to demonstrate whether specific binding to S2-6 in vitro expressed protein exists. If specific binding is shown, S2-6 DNA consensus sequence is characterized by the method described herein. To determine the region of S2-6 protein responsible for specific binding in vitro different peptide regions are expressed in the PET30 system followed by characterization of their DNA binding properties by the method described above.

S2-6 Northern Analyses

All known clones in Group I were carefully examined by Northern analysis, for transcript size and their relative expression levels in yHDF, sHDF and WS HDF. For the majority of these clones, abundance levels of mRNA were relatively low such that our initial Northern analysis performed on total RNA (10 μg) and polyA+RNA (1 μg) failed to reveal distinct bands. Therefore, Northern analysis was repeated using 3 μg of polyA+RNA obtained from larger expansions of these cell cultures. PolyA+RNA was isolated with the FastTrack kit (Invitrogen), which yielded high quality mRNA at approximately 1% of total RNA.

Northern analysis of S2-6 mRNA expression in young, senescent and Werner syndrome human fibroblasts is shown in FIG. 4. FIG. 4 is a photograph of a Northern gel showing S2-6 mRNA expression. Each lane contained 3 μg of polyA+ RNA. y—young, early passage; o—old, late passage human skin fibroblasts; W8-Werner syndrome skin fibroblasts. PolyA+RNA equality of loading and evenness of transfer to ZETA Probe nylon membrane were assessed by control hybridization with $^{32}$P end-labeled oligo-dT probe. A 2.1 kb transcript expressed in senescent and WS HDF was observed.

Northern blot analysis revealed that clone S2-6 hybridized exclusively to a 2.1 kb transcript expressed in senescent and WS HDF (FIG. 4) as well as young, nonproliferating, quiescent HDF (FIG. 5A) and is not expressed in immortal HeLa cells whether proliferating or quiescent (data not shown). Northern analysis of S2-6 mRNA expression in proliferating and nonproliferating normal human fibroblasts, e.g., growth arrested by confluency or starvation, is shown in FIGS. 5A and 5B. FIG. 5A is a photograph of a Northern gel of S2-6 mRNA expression under different growth conditions. Normal skin fibroblasts (A2 skin HDF at MPD26 (MPDmax-56)) logarithmically growing (L) in the presence of 15% FBS were made quiescent by contact inhibition after growing in the presence of 15% FBS for 6 days (C). Also, normal skin fibroblasts (A2 skin HDF at MPD26 (MPDmax-56)) logarithmically growing (L) in the presence of 15% FBS were made quiescent by serum depletion for 2 days (S). PolyA+RNA was isolated and 2 μg of RNA were loaded on each lane. For equal loading and evenness of transfer, the same filter was hybridized with GAPD (glyceraldehyde-3 phosphate dehydrogenase). A 2.1 kb transcript was observed in the non-proliferating fibroblast cells, whereas no transcript was observed in the logarithmically growing cells. These data suggest that expression of the S2-6 transcript is characteristic of normal cells with a diminished ability for proliferation.

FIG. 5B is a photograph of a Northern gel of S2-6 mRNA expression in transformed cell lines. Lanes 1 and 2 contained 2 μg of poly(A+)RNA derived from proliferating and confluent A2 HDF, respectively. Lanes 3–7 contained 10 μg of poly(A+)RNA derived from the following cell lines: (3) MRC5 fetal lung HDF transformed by SV40; (4) HTB140 melanoma metastatic to lymph node; (5) HTB40, adenocarcinoma, small intestine; (6) 293, kidney cells transformed by adenovirus; (7) CaCl, myeloma, bone marrow. Thus, FIG. 5B demonstrates that RNA expression in clone S2-6 is either abolished or significantly diminished in immortalized cell lines, whether they were immortalized by virus transfection or derived and established from primary tumors. These data suggest that expression of the S2-6 transcript is characteristic of normal cells with a diminished ability for proliferation.

FIG. 6A shows patterns of expression of the S2-6 and p21 mRNAs in quiescent fibroblasts stimulated to growth by 15% fetal bovine serum. The level of both transcripts increased shortly (1 hour) after releasing cells from quiescence, achieved maximum expression at 1 hour and were almost completely attenuated (especially the S2-6 transcript) when the DNA synthesis was initiated. The same blot was probed with GAPDH cDNA probe to examine RNA loading at each lane. FIG. 6B correlates the S2-6 expression (presented as a densitometric scan of Northern blot shown in FIG. 6A) and the DNA synthesis as an amount of $^3$H-thymidine incorporation into cells at different time points after cell stimulation. S2-6 mRNA was expressed exclusively at the early G1 phase and then its expression was suppressed when the DNA synthesis was initiated (S phase). Since patterns of expression of the S2-6 and p21 mRNAs are very similar, these data suggest that the S2-6 protein plays a similar during the cell cycle as the p21 protein, which has been identified as an inhibitor of clyclins.

Role S2-6 Plays in Inhibition of DNA Synthesis—Assay for Inhibition of DNA Synthesis This study was designed to determine the role S2-6 gene played in inhibition of DNA synthesis and/or cell growth. This was accomplished by microinjection of in vitro-synthesized antisense RNAs into young HDF and assessment of the level of DNA synthesis.

The protocol for assaying inhibition of DNA synthesis is as follows. Clones were selected based on their possible role in inhibition of DNA synthesis. Since clones isolated from the subtracted library contained only a partial sequence of their corresponding transcript, an indirect assay, e.g., microinjection of antisense RNA, was used to evaluate its possible effect on DNA synthesis. Thus, genes having a role in the inhibition of DNA synthesis would be expected to stimulate DNA synthesis. Based on previous experience with other clones which appeared to stimulate DNA synthesis despite its overexpression in senescent and quiescent cells, parallel experiments were performed to monitor inhibition of DNA synthesis after microinjection of antisense RNA. This study would indicate a stimulatory role of the cognate gene.

For this study, A25 normal skin HDFs approaching the end of their in vitro lifespan as measured by accumulated population doublings (56 from MPD$_{max}$=58, [$^3$H]-thymidine labeling index in the presence of 15% fetal bovine serum less than 15%), were grown in medium without serum for 5 days before microinjection. Thymidine labeling index at this time was less than 5%. Cells were microinjected with approximately 6000 copies of antisense RNA. Each sense RNA, hydrolyzed antisense RNA and water served as negative controls. Immediately after microinjection [$^3$H]-thymidine was added to the medium. In the assay for stimulation of DNA synthesis, cells remained in the conditioned serum-free medium, while in the assay for inhibition of DNA synthesis, cells were refed with medium supplemented with 15% FBS. Twenty four hours after microinjection cells were fixed and the number of labeled nuclei was counted in injected and noninjected cells. As a negative control, senescent human diploid fibroblast cells were injected with water.

Results of microinjection of antisense and sense RNA on DNA synthesis in nonproliferating human fibroblasts is shown in Table 3. Antisense and sense S2-6 mRNA were synthesized and capped in vitro using cDNA from partial S2-6 clone as a template. In repeated experiments, S2-6 showed stimulation of DNA synthesis after microinjection of antisense RNA, suggesting its possible function as an inhibitor of DNA synthesis (Table 3). Specifically, antisense RNA for clone S2-6 stimulated DNA synthesis approximately seven fold in injected cells when compared to uninjected cells. Moreover, by comparing the numbers of labeled nuclei present in the adjacent area to injected squares with those from a distant area, it was observed that this clone did not have a paracrine effect on neighboring cells. Also, S2-6 antisense RNAs did not inhibit DNA synthesis after refeeding injected cells by 15% FBS suggesting that S2-6 may have a role in stimulation of DNA synthesis.

Thus, these data, for the indirect functional assay, e.g., microinjection of antisense RNA, have shown that S2-6 is probably involved in the inhibition of DNA synthesis.

TABLE 3

EFFECT OF S2-6 mRNA MICROINJECTION
ON DNA SYNTHESIS IN SENESCENT HUMAN FIBROBLASTS

| RNA | Exp. No. | % labeled nuclei (no. of cells scored) injected | uninjected | Relative Stimulation |
|---|---|---|---|---|
| antisense | 1. | 17.9 (39) | 2.9(103) | 6.1 |
|  | 2. | 9.7 (72) | 1.4 (92) | 6.9 |
| sense | 3. | 8.0 (99) | 6.7 (73) | 1.2 |
|  | 4. | 7.3 (136) | 5.1(101) | 1.4 |
| water | 5. | 1.5 (133) | 0.8(131) | 1.8 |

The role S2-6 gene plays in inhibition of DNA synthesis and/or cell growth is also studied by transfection of young HDFs with an expression vector containing cDNA under the control of a strong constitutive promoter, such as the human cytomegalovirus promoter (CMV) followed by determination of the level of DNA synthesis in an assay for transient expression, and evaluation of colony formation and in vitro replicative lifespan as determined by Mean Population Doublings (MPD) in stable transformants.

S2-6 CDNA clone, isolated from cells undergoing a process of premature senescence, codes for a novel protein which contains specific zinc binding LIM domain. The 1.5 kb cDNA insert of this clone, entirely sequenced, codes for a new member of the LIM protein family. The putative protein deduced from the cDNA sequence contains on its C-terminus, a cysteine rich zinc binding domain (LIM domain) similar to those in a number of proteins with a role in development and regulation of transcription (Sadler, et al, 1992; Wang et al, 1992). LIM domain does not bind DNA; rather, it seems to act as an interface for protein-protein interactions (Schmeichel and Beckerle, 1994).

Members of recently emerging LIM protein family have a role in regulation of cell growth. The 2.1 kb S2-6 mRNA transcript is exclusively expressed in nonproliferating normal cells or normal cells with a diminished ability for proliferation and is not expressed in immortal cells (either transformed with virus or established tumor cell lines). Moreover, microinjection of antisense partial mRNA into nonproliferating human fibroblasts stimulates DNA synthesis, what indicates S2-6 role in inhibition of DNA synthesis. Thus, S2-6 protein is an inhibitor of DNA synthesis specifically expressed in nonproliferating cells.

Conclusions

Replicative senescence of human diploid fibroblasts (HDF) is a dominant trait, which predicts that overexpressed and/or newly expressed mRNAs, encoding negative growth regulatory functions, will be present in senescent compared to early-passage vigorously growing ("young") cells. The analysis of clones isolated from a subtracted WS cDNA library led to the identification of a novel cDNA, S2-6 that codes for a novel LIM protein. DNA sequence analysis of clone S2-6 cDNA revealed that its 1.5 kb insert codes for a novel protein "zinc binding" LIM domain.

Thus, S2-6 is a novel protein coded by complementary DNA clone discovered during the screening of a Werner syndrome cDNA library for overexpressed genes that may be involved in senescence of human fibroblasts. The data indicate that S2-6 CDNA clone codes for a novel LIM protein, specific for nonproliferating cells or whose expression is abolished or significantly diminished in immortalized or tumor derived cell lines, and has a function in inhibition of DNA synthesis. The data also indicate that the S2-6 gene sequence may play role in regulation of cell growth and differentiation. Thus, strategies of overexpressing S2-6 protein in cancerous cells may lead to inhibition of cell growth that is important in anti-cancer therapy.

Characterization of S2-6 cDNA Clone and Its Zinc Binding LIM Domain

Several experiments are outlined below that are specifically designed to further study the structure and function of the S2-6 protein. S2-6 protein belongs to the LIM protein family which consists of a variety of proteins with different function and cellular location. This protein may play a role in the inhibition of DNA synthesis. In order to clarify the mechanism of this inhibition, the cellular location of this protein is determined. A method of detection are employed for monitoring in situ expression and location of S2-6 protein as a fusion with green fluorescent protein as well as with immunocytochemistry using polyclonal antibodies. In the case of S2-6 nuclear location, which would indicate a role for S2-6 in regulation of transcription, DNA binding sequence for this protein will be determined. In the case of S2-6 cytoplasmic location, experiments leading to characterization of its interactions with other protein(s) and/or cell structure components (e.g. cytoplasmic membrane, stress fibers etc.) are studied.

Sequencing the Full Length S2-6 cDNA

Reconstruction of the full length S2-6 clone will include producing the 5' missing end of the 1.5 kb clone by using the 5' Rapid Amplification of cDNA Ends method (the 5' RACE method, commercially available from Gibco/BRL). Briefly, the 5' RACE system is a set of prequalified reagents intended for synthesis of first strand cDNA for subsequent PCR amplification. The method is based on the rapid amplification of cDNA Ends and anchored PCR methods and is suitable for the amplification of rare messages for which little sequence information is available. The 5' RACE system provides a rapid and reliable solution to a technically complex procedure.

The 5' RACE System involves the following: first strand cDNA is synthesized from total or poly(A)$^+$ RNA using a gene-specific primer (GSP1) that the user provides and SuperScript™ II, an RNase H derivative of Moloney murine leukemia virus reverse transcriptase (M-MLV RT). After first strand cDNA synthesis, the original mRNA template is destroyed with RNase H, which is specific for RNA:DNA heteroduplex molecules. Unincorporated dNTPs, GSP1, and proteins are separated with cDNA using a GlassMAX® spin cartridge. An anchor sequence is then added to the 3' end of the cDNA using TdT and dCTP. Since the tailing reaction is performed in a PCR-compatible buffer, the entire contents of the reaction may be directly amplified by PCR without intermediate organic extractions, ethanol precipitations, or dilutions. PCR amplification is accomplished using Taq DNA polymerase (Perkin-Elmer), a user-designed, nested gene-specific primer (GSP2) that anneals to a site located within the cDNA molecule, and a novel deoxyinosine-containing anchor primer provided with the system.

Following amplification, 5' RACE products can be cloned into an appropriate vector for subsequent characterization procedures, which may include sequencing, restriction mapping, preparation of probes to detect the genomic elements associated with the cDNA of interest, or in vitro RNA synthesis.

For obtaining the full length S2-6 clone the following steps will be performed: (1) Fragments produced by the 5' RACE method as described above will be ligated to the commercially available pGEMT vector which is specifically designed for ligation of PCR products. This protocol does not require blunt or cohesive ends. (2) Clones containing S2-6 fragments will be identified by employing the well known technique of colony hybridization. (3) The isolated positive clones identified by the colony hybridization protocol (Step 2 above) will then be examined for their size by restriction analysis using restriction enzymes, e.g., PstI and SphI. The clones will next be sequenced. (4) The newly identified S2-6 fragments will then be ligated into the originally isolated S2-6 clone (using known blunt end ligation techniques) and correctness of the open reading frame will be determined by employing standard DNA sequencing methods.

Kinetics of S2-6 Gene Expression During Cell Cycle

To clarify whether the expression of S2-6 is dependent on other events in addition to those that are growth inhibitory or senescence-specific, steady-state levels of its RNAs during the cell cycle are determined. Cells will be synchronized by a double thymidine block which will arrest them at the Gl/S border (Lew, et al. 1991). Cells are released from the block by refeeding with medium containing thymidine. Progression through the cell cycle will be measured by the fluorescence-activated cell sorting (FACS) technique and RNA are isolated every 3 hours after release. Additionally, transition through different phases in the cell cycle will be monitored by Northern analysis to determine the expression of two reference mRNAs (cyclin E and cyclin Bl) whose expression is regulated by the cell cycle. Cyclin E mRNA is expressed in late G1 and disappears by late S phase (Lew, et al. 1991), whereas cyclin B1 mRNA is expressed in S phase and no longer seen in M (Pines, et al. 1989; Gyuris, et al. 1993).

Due to the low abundance of transcripts to be studied and the high costs of growing large amounts of cells for polyA+ RNA isolation, RNA samples collected in the above experiments are analyzed by competitive quantitative RT-PCR which is several orders of magnitude more sensitive than traditional Northern blotting and RNase protection techniques (Wang, et al. 1989; Quantitative RT-PCR 1993). Based on sequence data for S2-6 cDNA clone, primers will be designed at a distance of approximately 200–500 nucleotide apart to minimize the difficulties associated with PCR amplification of longer DNA fragments. A region is selected, as determined from its cDNA sequence, that does not form strong secondary structures (e.g. palindromic structures) nor consists of a high GC content, and stretches of continuous guanine or cytosine bases will be avoided; these factors can drastically diminish dramatically efficiency of the PCR reaction. To correct for tube-to-tube variations in amplification efficiency, exogenously added internal amplification standard differing slightly in size (approximately 50 nucleotides) from the target sequence are used, which will enable one to distinguish between the amplified (target and standard) sequences (Wang, et al. 1989). Thus, competitive PCR experiments can be performed where both target and standard sequences are amplified from the same primers to minimize differences in the amplification efficiencies of these sequences. Another advantage of using an exogenous standard instead of an endogenous mRNA, e.g. β-actin, as a standard, is that one can manipulate its concentration in the reaction mixture to obtain concentrations closer to those of the target sequence, thereby minimizing the possibility of interference with amplification of target RNA. Reactions will also be run with and without reverse transcriptase to control for amplification of residual contaminating DNA.

Additional Microinjection and Functional Analyses of S2-6

As discussed above, microinjection experiments were performed and antisense RNAs were used to eliminate complementary transcripts of S2-6 overexpressed in senescent HDF. To confirm the inhibitory effect of S2-6 on DNA synthesis and cell growth, "short-term" and "long-term" functional assays are performed. In the short term assay, in vitro synthesized full-length sense mRNA is microinjected into fetal HDF transformed by SV40 antigen (MRC5 strain). Cells are made quiescent by incubation for five days in medium without fetal bovine serum (FBS), and then injected with approximately 6000 mRNA copies, a standard range used to effect overexpression. Microinjected cells are refed after injection with fresh medium containing 15% FBS plus $^3$H-thymidine. Twenty four hours after microinjection and exposure to $^3$H-thymidine, cells are fixed and DNA synthesis determined by scoring labeled nuclei in injected versus uninjected cells (Liu, et al. 1994; Lecka-Czernik, et al. 1995). As negative controls, cells are microinjected with (1) water, (2) hydrolyzed RNA and (3) full length neutral transcript, such as WS3-10, which is known from experiments not to have an effect on DNA synthesis (Goldstein, et al. 1989).

DNA synthesis as reflected by [$^3$H]-thymidine uptake is studied in cells transfected with the episomal mammalian expression vector pCEP4 (Invitrogen) where expression of the S2-6 cDNA is under the control of a constitutive CMV enhancer-promoter (for the immediate-early gene of the human cytomegalovirus) providing a high-level of protein expression. As a control for DNA synthesis, [$^3$H]-thymidine uptake will be monitored and analyzed in cells transfected with "empty" (without cDNA insert) vector.

Cells are transfected by electroporation which is routinely used and usually yields approximately 40% transfection efficiency. The efficiency of transfection in each experiment is estimated by cotransfection with pCEP4 vector containing a cDNA insert coding for β-galactosidase. β-galactosidase production is monitored by cytochemical analysis, using Galacto-Light™ (TROPIX, Inc.) a chemiluminescent detection method, an easy and extremely sensitive assay enabling detection of 2 μg to 20 ng of β-galactosidase. Measurements of β-galactosidase activities in transfectants will be standardized by comparing the level of endogenous enzyme in non-transfected cell extracts from young and old HDF. Light output generated by cleavage of Galacton™ chemiluminescent substrate by β-galactosidase will be quantitatively measured using a luminometer.

In the "long term" assay, by selection to hygromycin resistance, colonies with stable integrants are isolated to reveal the effects of continuous overexpression of these cDNA clones on DNA synthesis and cell growth in yHDF. If S2-6 has an immediate effect on inhibition of DNA synthesis, then one can expect difficulties in obtaining stable transfectants, which is reflected by a significant difference in yields of stable transfectants with or without insert. In the case of a delayed inhibitory effect (e.g. an effect on cell proliferation) one can expect a similar number of stable transformants but their rate of cell proliferation and lifespan as determined by Mean Population Doublings (MPD) are reduced in cells transfected with cDNA clone S2-6 in contrast to those transfected with "empty" plasmid. A parallel experiment is done where the cDNA sequences is introduced in antisense direction. In this case, one can expect the adverse effect. If these genes have a role in restricting MPDs one can expect an increase in the $MPD_{max}$ of these stable transfectants.

To determine whether the isolated stable transfectants express the RNA and protein of interest, a recently developed method where cognate protein is expressed as a fusion with green fluorescent protein (GFP) is utilized. GFP is under the control of the cytomegalovirus promoter (CMV) and neomycin is a selection marker for stable transfectants (Clontech). GFP protein expression will be identified in situ upon UV or blue light activation of GFP chromophore which generates green fluorescent light (Chalfie, et al. 1994). This method allows easy and direct detection of colonies expressing the transfected protein. As an additional functional assay, senescent HDF cells will be microinjected with polyclonal antibodies raised against S2-6 protein. Appropriate preimmune globulins will serve as controls. With this assay, the activity of each cognate protein may be blocked and the subsequent effect on DNA synthesis is monitored and analyzed.

Determination of Protein Level and Location: Polyclonal Antibody Production To Determine Location and Level of Protein Expression To characterize the cognate S2-6 protein in yHDF and sHDF, polyclonal antibodies are produced in rabbits using as antigen a fusion protein expressed in the *E. coli* pET30 system (Novagen). Thus, polyclonal antibodies are produced against S2-6 to compare levels of protein expression and cellular location in young and senescent HDF. In pET30 (Novagene) system, the S2-6 cDNA insert is placed under the control of strong bacteriophage T7 transcription and translation signals which after induction yields the desired peptide in large quantities. The short oligohistidine (His-Tag) stretch on the N-terminus of the fusion protein binds to divalent cations allowing one step affinity purification on Ni-bound agarose. S2-6 cDNA insert is cloned into the multicloning region, downstream of the T7 promoter sequence, AUG transcription initiation codon and His-Tag coding sequence. DNA sequencing analysis is performed to determine that the proper open reading frame (ORF) is correctly aligned in the S2-6/pET30 construct. Chimeric protein is expressed in BL21(DE3)pLysS *E. coli* strain after IPTG induction of the lacUV5 promoter that controls the expression of T7 polymerase, the enzyme responsible for the expression of fusion protein. Previously, a similar system (pET19) was used to express WS3-10 protein from a cDNA clone isolated from the unsubtracted WS cDNA library (Grigoriev, et al. 1996) followed by protein purification and production of specific WS3-10 polyclonal antibodies in rabbits. Polyclonal antibodies used in Western blotting, immunoprecipitation of $^{35}$S-methionine-labeled proteins (Grigoriev, et al. 1994) and immunocytochemistry (Grigoriev, et al. 1996) will enable the quantification and localization of the S2-6 protein in cells. Thus, the level of S2-6 protein in young versus old cells is examined, and the amount of cognate proteins under different growth conditions such as inhibition by serum depletion and stimulation by serum repletion is quantified. To detect possible post-translational modifications (e.g., glycosylation, phosphorylation on proteolytic cleavage), the electrophoretic mobility of the cognate cellular protein from old and young cells is compared with that which is translated in rabbit reticulocyte lysates (Lecka-Czernik, et al. 1995).

Assessment of S2-6 Protein DNA Binding Properties

As previously stated above, the S2-6 putative protein contains one LIM domain which consists of two types of "zinc fingers": $C_2H_2$ and $C_2C_2$. DNA sequence analysis using the GenBank Database for transcription factors revealed that this protein contains no homeodomain determined to be a transactivation domain, however the region between amino acids 170–200 does show significant homologies to known transcription factors.

Because of the present controversy about the DNA binding ability of LIM domains (42), the presence of a $C_2H_2$ zinc binding domain highly homologous to those present in transcription factors (see FIG. 7), and homologies in the region outside the LIM domain to protein sequences of known transcription factors like the H15 homeobox-containing gene from the honeybee and E2 from human papillomavirus (92, 93), determining whether this S2-6 protein can specifically bind to DNA is essential. FIG. 7 is a schematic representation showing an alignment of several "zinc finger" sequences: S2-6 "zinc finger," part of LIM domain; three zinc finger domains from clone S1-3; *D. melanogaster* hunchback protein; mkr3, murine Kruppel-like protein; and cKrl, chicken Kruppel-like protein. The bottom line represents the sequence for the S2-6 "zinc finger", part of LIM domain. Amino acids involved in zinc binding are boxed by solid lines; highly conserved amino acids are boxed by dotted lines. The consensus for DNA binding sequence specific for S2-6 protein is determined using an affinity selection of DNA sequences from a library of synthetic random nucleotides. A synthetic random oligonucleotide library is used to demonstrate whether S2-6 protein can function as a DNA binding protein and will also be used to characterize the DNA binding site for S2-6.

Construction of a Degenerative Oligonucleotide Library

A library of degenerative oligonucleotides are constructed according to Morris, et al. (Morris, et al. 1994). Such a library was used for determination of a DNA consensus sequence for MZF1, a member of the $C_2H_2$ "zinc finger" protein family, that plays a central role in regulation of hematopoiesis. A 45-mer oligonucleotide library containing a 14-base random sequence flanked by EcoRI and BamHI linkers is synthesized by the Molecular Biology Core facility at University of Arkansas Medical Sciences. Two primers are also synthesized, one complementary to the 3' linker and the other identical to the 5' linker. The synthetic template and 3' primer is radiolabelled with T4 polynucleotide kinase and [$^{32}$P]ATP and used in a primer extension reaction with Vent polymerase (New England Biolabs). Gel purified double-stranded radioactively labeled DNA molecules are used to test S2-6 protein-DNA binding activity in electrophoretic mobility shift assay and in the functional selection of S2-6 protein DNA binding site.

Determination of Consensus Sequence for S2-6 Binding

To understand the function and biological relevance of a new transcription factor it is critical to identify the target DNA-binding site. Analysis of the crystal structure of the "zinc finger" proteins with their cognate DNA-binding sites revealed that "zinc finger" domains recognize a 3-nucleotide sequence present on either one or both strands in the major groove of the DNA helix. Currently, the specific DNA consensus binding sites have been determined for few members of the "zinc finger" protein family and these never exceed 9 nucleotides (Morris, et al. 1994; Letovsky, et al. 1989; Christy, et al. 1989; Rauscher, et al.; Kinzler, et al. 1990).

For selection of DNA sequences that interact with S2-6 protein, the method for selection of trp repressor binding sequences are followed (Hurlburt, et al. 1992). Briefly, in vitro expressed S2-6 protein is coupled to an AminoLink agarose column. A mixture of $^{32}$P-end-labeled random oligonucleotides is retained by S2-6 protein in low salt conditions to favor specific interaction. DNAs specifically bound to S2-6 protein is recovered by high salt elution followed by PCR amplification. Several rounds (3–5) of binding and PCR amplification is performed to enrich a pool of specifically bound sequences. The efficiency of such enrichment is monitored by determining the amount of the radioactivity retained (by scintillation counting) versus the total amount of radioactivity loaded onto the column in each step of selection. When no increase in the specifically bound DNA is observed, a statistically relevant amount of retained DNA molecules (approximately 100) is cloned and sequenced. A consensus binding site for S2-6 protein is determined using the University of Wisconsin Genetics Computer Group's (GCG) DNA sequence analysis programs running locally on a VAX.

Determination of Binding Affinity by the Apparent Equilibrium Dissociation Constants Using an electrophoretic mobility shift assay (EMSA), the equilibrium dissociation constant ($K_D$) is determined describing binding affinity of S2-6 protein to the selected consensus DNA sequences. The apparent equilibrium dissociation constant ($K_D$) is determined for selected oligonucleotides and in vitro-synthesized consensus sequence using the electrophoretic mobility shift assay—EMSA (Morris, et al. 1994; Czernik, et al. 1994; Ausubel, et al. 1993). This comparison will enable the selection of sequences with the highest binding affinities. A limiting amount of DNA is titrated with various concentrations of S2-6 protein and DNA-protein complexes is analyzed by native polyacrylamide gel electrophoresis. The $K_D$ value, equal to the concentration of the analyzed protein required to bind half of the available DNA (Riggs, et al. 1970; Hurlburt, et al. 1992), is determined by quantitative densitometric analysis of the autoradiograms and will be considered as the KD as described in Czernik, et al. 1994.

Determination of S2-6 Protein Role in Regulation of Gene Expression—Assessment of S2-6 Protein as a Transcription Factor Experiments presented below define the function of S2-6 as a transcription factor and lead to the isolation of "downstream" gene sequences regulated by it. To study S2-6 as a transcription factor, genomic elements that interact with S2-6 protein is identified and characterized. Genes which may be regulated by the S2-6 protein is studied by searching for homologies between established S2-6 DNA-binding sequence and sequences in DNA computer databases known to bind transcription factors. DNA is also isolated from a genomic library of DNA ("cis-acting") fragments which specifically bind to S2-6 ("trans-acting") protein and their role as transcription regulatory elements is studied using a luciferase promoter/enhancer reporter system. This system also is used to look for differences in regulation of transcription between young and senescent HDF.

More specifically, the Genbank/EMBL databases are searched for homologies of established consensus and selected sequences with the highest KD values to DNA sequences known to bind transcription factors. The natural DNA sequences that specifically bind the S2-6 protein are also studied. Human genomic DNA is digested into small fragments and linkers harboring specific primer sequences to enable PCR is ligated to their ends. DNA fragments which will specifically bind S2-6 protein are selected using methods described above. Selected fragments are cloned, sequenced, and S2-6 protein binding affinity determined.

Those selected sequences with the highest binding affinity are analyzed for their potential to function as transcriptional regulatory elements using the luciferase promoter-enhancer reporter system (GeneLight™, Promega). With different types of GeneLight plasmids, each carrying the coding region for firefly (*Photinus pyralis*) luciferase which is used to monitor transcriptional activity in transfected eucaryotic cells, selected DNA fragments will be examined for their possible function as a promoter, enhancer or attenuator of transcription. Isolated genomic sequences with S2-6 protein binding affinity are introduced into different types of GeneLight plasmids, and the luciferase activity in transfected young and senescent fibroblasts is determined by a specific assay (Promega). This assay is approximately 100 times more sensitive than the CAT assay and is very suitable, especially for weak promoters. Sequences regulated differently in sHDF versus yHDF are identified and studied (this system has been used to study the enolase gene enhancer region (Taylor, et al. 1995).

Isolation of "Downstream" Gene Sequences Regulated by S2-6 Protein

Gene sequences regulated by S2-6 protein are isolated by comparing the pool of transcripts from cells induced to express S2-6 protein with the pool of transcripts from uninduced cells. Once S2-6 protein is identified as a potential transcription factor and genomic DNA sequences specifically interacting with this protein are isolated, experiments leading to the isolation of "downstream" genes regulated by S2-6 protein are performed. Depending on the role of genomic regulatory elements (promoter/enhancers or attenuators, determined in above experiments) routes described below are pursued.

In general, the pool of RNA transcripts isolated from cells forced to overexpress S2-6 protein are compared with the pool of transcripts isolated from uninduced cells which represent the basal level of naturally occurring messages. S2-6 cDNA are cloned into the LacSwitch Inducible Mammalian Expression System (available from Stratagene), where transcription of the inserted gene sequence is blocked by binding of Lac-repressor protein to Lac-operator sequences located upstream of the inserted gene. Transcription and expression of S2-6 protein are triggered by IPTG which decreases binding affinity of the Lac-repressor protein to operator sequences. The LacSwitch System seems to be especially useful for induction of a gene sequence whose transcript is expressed at a very low level and its tight regulation is extremely important. This experiment will use HSC172 cells which lack S2-6 expression. Transfected fibroblasts are selected by their hygromycin and G418 resistance. The fraction of transformants able to express S2-6 protein after IPTG induction is determined by immunocytochemistry using polyclonal antibodies against S2-6 protein. Two pools of poly($A^+$) RNA are isolated: (1) one pool isolated from transfected cells induced by IPTG to express S2-6 protein, and (2) a second pool isolated from the same uninduced cells. One pool will serve as a template for construction of a cDNA library, the other will be used for subtraction of this library to isolate cDNA sequences which are regulated by S2-6 protein, the procedure previously utilized for construction of the subtracted WS cDNA library. Should the data obtained from the luciferase assay described above indicate that S2-6 functions as a positive regulator of transcription, a library from induced cells are constructed and subtracted with poly(A+)RNA from uninduced cells. Additionally, the library is subtracted with in vitro transcribed RNA for S2-6 gene sequence to avoid isolation of the corresponding cDNA clones. If S2-6 is expected to be a negative regulator of gene expression, the cDNA library is constructed from the uninduced pool of poly(A+)RNA and subtracted with an induced pool. Isolation of cDNA clones specifically regulated by S2-6 protein will be followed by their structural analysis.

Assessment of Protein-Protein Interactions

Interactions of S2-6 protein with other cellular protein(s) is determined by immunoprecipitation of $^{35}S$ in situ radiolabeled proteins followed by SDS-PAGE analysis (112). Comparisons will be made between the interactions of young HDF, senescent HDF, growth inhibited cells (either by serum depletion or contact inhibition), and conditions that stimulate S2-6 mRNA expression, to determine whether qualitative differences exist among these various conditions.

The following references may facilitate the understanding or practice of certain aspects and/or embodiments of this invention. Inclusion of a reference is this list is not intended to and does not constitute an admission that the reference represents prior art with respect to the present invention.

Amaravadi, et al., *Biotechniques*, 16:98–103 (1990).
Arber, et al., *Cell*, 79:221–231.
Argaves, et al., *J. Cell Biol.*, 111:3155–3164 (1990).
Ausubel, et al., *Current Protocols in Molecular Biology*, Vol. II, Greene Publishing Associates and John Wiley and Sones (1993).
Benn, et al., *Gene*, 106:207–212 (1991).
Bernard, et al., *Cell Growth Differ.*, 5:1159–1171 (1994).
Bevilacqua, et al., *Cancer Res.*, 49:5185–5190 (1989).
Call, et al., *Cell*, 60:509–520 (1990).
Chalfie, et al., *Science*, 263:802–805 (1994).
Chomczynski, et al., *Anal. Biochem.*, 162:156–159 (1987).
Chowdhury, et al., *Nucleic Acids Res.*, 16:9995–10011 (1988).
Christy, et al., *Proc. Nat'l. Acad. Sci, U.S.A.*, 6:8737–8741 (1989).
Church, et al., *Proc. Natl. Acad. Sci. USA*, 81:1991–1995 (1984).
Cristofalo, et al., *Physiol. Rev.*, 73:617–638 (1993).
Czernik, et al., *J. Biol. Chem.* 269:27869–27875, 1994.
DeTata, et al., *Exp. Cell Res.*, 205:261–269 (1993).
Dice, et al., *Physiol. Rev.*, 73:149–159 (1993).
Dimri, et al., *Exp. Cell Res.*, 212:132–140 (1994).
Dimri, et al., *J. Biol. Chem.*, 269:16180–16186 (1994).
Dje, et al., *Nucleic Acid Res.*, 18:3489–3493 (1990).
Doolittle, et al., *Nature*, 307:558–560 (1984).
Duguid, et al., *Proc. Natl. Acad. Sci. USA*, 85:5738–5742 (1988).
Dulic, et al., *Proc. Natl. Acad. Sci. USA* 90:11034–11038 (1993).
Dulic, et al., *Cell*, 76:1013–1023 (1994).
El-Deiry, et al., *Cell*, 75:817–825 (1993).
Epstein, et al., *Medicine*, 45:177–221 (1966).
Fett, et al., *J. Biol. Chem.*, 266:1448–1455 (1991).
Flemington, et al., *Proc. Natl. Acad. Sci. USA*, 90:6914–6918 (1993).
Freyd, et al., *Nature*, 344:876–879 (1990).
Funk, et al., *Pro. Natl. Acad. Sci. USA*, 88:2648–2652 (1991).
Gilles, et al., *J. Biol. Chem.*, 266:8784–8789 (1991).
Goldstein S.; The Biology of Aging, in *Textbook of Internal Medicine*, Section Ed, W. R. Hazzard, J. B. Lippincott, Phil., 2nd ed, pp. 2336–2342 (1992).
Goldstein, et al., *Science*, 249:1129–1133 (1990).
Goldstein S.; Cellular senescence. In: Endocrinology, 2nd Ed., L. J. DeGroot, et al. eds. Grune and Stratton, New York, pp. 2525–2549 (1989).
Goldstein, et al., *Exp. Cell Res.* 70:436–439 (1971).
Goldtein, S.; Human genetic disorders which feature accelerated aging. In: *The Genetics of Aging*, E. L. Schneider, ed., Plenum Press, New York, pp. 171–224 (1978).
Goldstein, et al., *Exp. Gerontol,* 24:461–468 (1989).
Goldstein, et al., *J. Cell Physiol.*, in press (1994).
Goldstein, et al., *J. Cell Physiol.*, 156:294–302 (1993).
Goto, et al., 8. *Nature*, 355:735–738 (1992).
Grigoriev, et al., *Exp. Cell Biol.*, 219:315–321 (1995).
Grigoriev, et al., *J. Cell Physiol.* 160:203–211 (1994).
Grigoriev, et al., *Exp. Gerontol,* 31:145–157 (1996).
Gyuris, et al., *Cell*, 75:791–803 (1993).
Hall, et al., *Mol. Cell Biol.*, 13:4986–4998 (1993).
Hara, et al., *J. Biol. Chem.* 269:2139–2145 (1994).
Harley, et al., *J. Cell. Physiol.*, 97:509–516 (1978).
Harper, et al., *Cell*, 75:805–816 (1993).
Hayflick, et al., *Exp. Cell Res.*, 37:614–636 (1965).
Hirsch-Behnam, et al., *Virus Res.* 18:81–97 (1990).
Hunter T.; Braking the cycle. *Cell*, 75:839–841 (1993).
Hurlburt, et al., *J. Biol. Chem.*, 267:16783–16789 (1992).
Inoue, et al., *Proc. Natl. Acad. Sci.*, 90:11117–11121 (1993).
Jarvis, et al., *Proc. Natl. Acad. Sci. USA*, 91:73–77 (1994).
Jelinek, et al., *Annu. Rev. Biochem.*, 51:813–844 (1982).
Joseph, et al., *Proc. Nat'l. Acad. Sci., U.S.A.,* 85:7164–7168 (1988).
Kadonaga, et al., *Cell*, 51:1079–1090 (1987).
Kanzaki, et al., *Cell*, 61:1051–1061 (1990).
Karlsson, et al., *Nature*, 344:879–882 (1990).
Kaziro, et al., *Biochim. Biophys. Acta*, 505:95–127 (1978).
Kenyon, et al., *Science*, 253:802 (1991).
Kenyon, et al., *J. Biol. Chem.*, 268:18437 (1993).
Kiess, et al., *Oncogene*, 10:61–68 (1995).
Kinzler, et al., *Mol. Cell Biol.* 10:634–642 (1990).
Klug, A. and Rhodes, D.; Zinc fingers: a novel protein fold for nucleic acid recognition. *Cold Spring Harbor Symposia on Quantitative Biology*, 52:473–482 (1987).
Koff, et al., *Science*, 260:536–539 (1993).
Kolesnick, et al., *Cell*, 77:325–328 (1994).
Kornblihtt, et al., *Proc. Natl. Acad. Sci. USA*, 80:3218–3222 (1983).
Koths, et al., *J. Biol. Chem.*, 268:14245–14249 (1993).
Kozak, et al., *J. Cell Biol.*, 115:887–903 (1991).
Krieg, et al., *Nucleic Acid Res.*, 12:7057–7070 (1984).
Lecka-Czernik, et al., *Mol. Cell Biol.*, 15:120–128 (1995).
Lecka-Czernik, et al., *Exp. Gerontology,* 31:159–174 (1995).
Lee, et al., *J. Biol. Chem.*, 268:24453–24459 (1993).
Letovsky, et al., *Nucleic Acids Res.*, 17:2639–2652 (1989).
Lew, et al., *Cell*, 66:1197–1206 (1991).
Liotta, et al., *J. Natl. Cancer Instit.*, 82:1170–1173 (1990).
Liu, et al., *Proc. Natl. Acad. Sci. USA*, 91:2186–2190 (1994).
Lumpkin, et al., *Science*, 232:393–395 (1986).
Maniatis, et al., *Molecular Cloning: A laboratory Manual,* 2nd ed. Cold Spring Harbor Lab., Cold Spring Harbor, N.Y. (1989).
Mann, et al., *EMBO J,* 8:65–72 (1989).
Maslen, et al., *Nature*, 352:334–337 (1991).
Moerman, et al., *Exp. Gerontal,* 28:361–370 (1993).

Moldave, et al., *Annu. Rev. Biochem.*, 54:1109–1149 (1985).
Morris, et al., *Mol. Cell. Biol.*, 14:1786–1795 (1994).
Moses, et al., *Cell*, 63:245–247 (1990).
Murano, et al., *Mol. Cell Biol.*, 11:3905–3914 (1991).
Nada, et al., *J. Biol. Chem.*, 268:7660–7667 (1993).
Nevins, J. R.; A closer look at E2F. *Nature*, 358:375–376 (1992).
Noda, et al., *Exp. Cell Res.*, 211:90–98 (1994).
Norwood, et al., *Proc. Natl. Acad. Sci. USA*, 71:2231–2235 (1974).
Norwood, T. H., Smith, J. R., and Stein, G. H.; Aging at the cellular level: the human fibroblastlike cell model. In: *Handbook of Biology of Aging*, E. L. Schneider and J. W. Rowe, eds., 3rd ed., pp. 131–154, (1990).
Obeid, et al., *Clin. Res.*, 42:114 (1994).
Obeid, et al., *Science*, 259:1769–1771 (1993).
Ohaski, et al., *J. Biochem., (Tokyo)* 116:636–642.
Okayama, et al., *Methods Enzymol.*, 154:3–28 (1987).
Panayotou, et al., *Cell*, 56:93–101 (1989).
Pathak, et al., *Cell*, 54:633–639 (1988).
Penttinen, et al., *Proc. Natl. Acad. Sci. USA*, 85:1105–1108 (1988).
Peters, et al., *Cell*, 79:181–184 (1994).
Pines, et al., *Cell*, 58:833–846 (1989).
Polyak, et al., *Genes & Development*, 8:9–22 (1994).
Polyak, et al., *Cell*, 78:59–66 (1994).
Ponte, et al., *Nucleic Acids Res.*, 12:1687–1689 (1984).
Ptashne, et al., *Nature*, 335:683–689 (1988).
Quantitative RT-PCR. In: *Methods and Application, Book 3*, ed., CLONTECH Laboratories, Inc. (1993).
Rasoamanantena, et al., *Exp. Cell Res.* 213:121–127 (1994).
Rauscher, et al., *Science*, 250:1259–1262.
Reed, et al., *J. Cell Physiol.*, 158:169–179 (1994).
Riabowol, et al., *Proc. Natl. Sci. Acad. USA*, 89:157–161 (1992).
Richter, et al., *Cancer Res.*, 51:6010–6013 (1991).
Ridley, et al., *Cell*, 70:401–411 (1992).
Riggs, et al., *J. Mol. Biol.*, 48:67–83 (1970).
Roberts, et al., *J. Biol. Chem.*, 263:4586–4592 (1988).
Rooney, et al., *Gene*, 71:439–449 (1988).
Ruoslahti, et al., *Cell*, 64:867–869 (1991).
Sadler, et al., *J. Cell Biol.*, 119:1573–1587 (1992).
Sakamoto, et al., *J. Biol. Chem.*, 266:3031–3038 (1991).
Salk, D *Hum. Genet.*, 62:1–5 (1982).
Sanchez-Garcia, et al., *Trends Genet.*, 10:315–320 (1994).
Sanger, et al., *Proc. Natl. Acad. Sci. USA*, 74:5463–5467 (1977).
Schellenberg, et al., *Lancet*, 339:1002 (1992).
Schmeichel, et al., *Cell*, 79:211–219 (1994).
Schweinfest, et al., *Genet Annal. Techn. Appl.*, 7:64–70 (1990).
Schuchman, et al., *J. Biol. Chem.*, 266:8531–8539 (1991).
Serrano, et al., *Nature* 366:704–707 (1993).
Seshadri, et al., *Science*, 247:205–209 (1990).
Shibanuma, et al., *J. Biol. Chem.*, 269:26767–26774 (1994).
Shina, et al., *Science*, 266:282–285 (1994).
Show, et al., *Cell*, 46:659–667 (1986).
Shutze, et al., *Cell*, 71:765–776 (1992).
Sive, et al., *Nucleic Acid Res.*, 16:10937 (1988).
Stahl, et al., *Cancer Res.*, 52:445–449 (1991).
Steeg, et al., *J. Natl. Cancer Inst.*, 80:200–204 (1988).
Stein, et al., *Science*, 249:666–669 (1990).
Stein, et al., *Proc. Natl. Acad. Sci. USA* 88:11012–11016 (1991).
Stein, et al., *Proc. Natl. Acad. Sci. USA*, 78:3025–3029 (1981).
Sukhatme, et al., *Cell*, 56:337–343 (1988).
Swaroop, et al., *Genomics*, 2:37–47 (1988).
Symington, B. E.; *J. Biol. Chem.*, 267:25744–25747 (1992).
Tanaka, et al., *Exp. Cell Res.*, 127:185–190 (1980).
Tatsuka, et al., *Nature*, 359:333–336 (1992).
Tautz, et al., *Nature*, 327:383–389 (1987).
Taylor, et al., *J. Biol. Chem.*, 270:2535–2540 (1995).
Termin, J. D.; *Exp. Gerontol*, 25:217–221 (1990).
Thweatt, et al., *Biochem. Biophys. Res. Commun.*, 187:1–7 (1992).
Thweatt, et al., *BioEssays*, 15:421–426 (1993).
Toyoshima, et al., *Cell*, 78:67–74 (1994).
Uetsuki, et al., *J. Biol. Chem.*, 264:5791–5798 (1989).
Walldorf, et al., *Proc. Nat'l. Acad. Sci., U.S.A.*, 86:9971–9975 (1990).
Wang, et al., *Proc. Nat'l. Acad. Sci., U.S.A.*, 86:9717–9721 (1989).
Wang, et al., *Cancer Res.*, 53:717–720 (1993).
Wang, et al., *J. Biol. Chem.*, 267:9176–9184 (1992).
Way, et al., *Cell*, 54:5–16 (1988).
Wharton, et al., *Cell*, 43:567–581 (1985).
Witzgall, et al., *Mol. Cell. Biol.*, 13:1933–1942 (1993).
Xiong, et al., *Nature*, 366:701–704 (1993).
Yanishevsky, et al., *Exp. Cell Res.*, 126:469–472 (1980).

What is claimed is:

1. A substantially pure DNA encoding a protein comprising SEQ ID NO: 2.

2. The DNA of claim 1, wherein said DNA comprising a sequence of at least 20 consecutive nucleotides of the region from nucleotides 1 to 1029 of SEQ. ID. NO:1.

3. The substantially pure DNA of claim 2 comprising a sequence of at least 20 consecutive nucleotides of the region encoding the zinc binding LIM domain of SEQ. ID. NO:3.

4. The DNA of claim 1, wherein said protein is a human zinc binding LIM-only protein S2-6.

5. A vector comprising the DNA of claim 4.

6. The DNA of claim 4, wherein said DNA is operably linked to regulatory sequences for expression of said protein, said regulatory sequences comprising a promoter.

7. A cell comprising the DNA of claim 6.

8. An essentially homogeneous population of cells, each of which comprises the DNA of claim 6.

* * * * *

```
                         SEQUENCE LISTING (1) GENERAL INFORMATION:

(iii) NUMBER OF SEQUENCES:   3

(2) INFORMATION FOR SEQ ID NO:1:

(i) SEQUENCE CHARACTERISTICS:
         (A) LENGTH:   1549 bp
         (B) TYPE:   nucleic acid
         (C) STRANDEDNESS:   single-stranded
         (D) TOPOLOGY:   linear (ii) MOLECULE TYPE:
         (A) DESCRIPTION:   c-DNA (iii) HYPOTHETICAL:   NO
```

(iv) ANTI-SENSE: NO (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 1:

```
GTCAGCAAGA GGTGTGGCAT GTTTGGGATG CAAGGGGACG TGTTCGGGCT TCGAGCACAT          60
TCATGGAGGA AAATATGCAA GTCTTGCAAA TGCAGCCAAG AGGACCACTG CCTAACATCT         120
GACCTAGAAG ACGATCGGAA AATTGGCCGC TTGCTGATGG ACTCCAAGTA TTCCACCCTC         180
ACTGCTCGGG TGAAAGGCGG GGACGGCATC CGGATTTACA AGAGGAACCG GATGATCATG         240
ACCAACCCTA TTGCTACTGG GAAAGATCCC ACTTTTGACA CCATCACCTA CGAGTGGGCT         300
CCCCCTGGAG TCACCCAGAA ACTGGGACTG CAGTACATGG AGCTCATCCC CAAGGAGAAG         360
CAGCCAGTGA CAGGCACAGA GGGTGCCTTT TACCGCCGCC GCCAGCTCAT GCACCAGCTC         420
CCCATCTATG ACCAGGATCC CTCGCGCTGC CGTGGACTTT TGGAGAATGA GTTGAAACTG         480
ATGGAAGAAT TTGTCAAGCA ATATAAGAGC GAGGCCCTCG GCGTGGGAGA GTGGCCCTC          540
CCGGGCAGGG TGGCTTGCCC AAGGAGGAGG GGAAGCAGCA GGAAAAGCCA GAGGGGGCAG         600
AGACCACTGC TGCTACCACC AACGGCAGTC TCAGTGACCC GTCCAAAGAA GTGGAATACG         660
TCTGCGAGCT CTGCAAGGGA GCGGCCCCTC CTGACAGCCC CGTGGTCTAC TCGACAGGGC         720
AGGCTACAAC AAGCAGTGGC ACCCCACCTG CTTTGTGTGT GCCAAGTGCT CCGAGCCGCT         780
GGTGGACCTC ATCTACTTCT GGAAGGATGG TCACCCTGGT GCGGCCGCCA TTACTGCGAG         840
AGTCTGCGGC CCCGGTGCTC CGGCTGCGAT GAGATAATAT TCGCTGAGGA CTACCAGCGT         900
GTGGAAGATC TGGCCTGGCA CCGAAAGCAC TTTGTCTGTG AGGGTTGTGA GCAGCTGCTG         960
AGCGGCCGGG CGTACATCGT CACCAAGGGT CAGCTTCTGT GCCCAACTTG CAGCAAGTCC        1020
AAACGCTCCT GAAGGGCTGC CCACCCACAG CCAGAATCCA CAGGATCCCA CCGAGAAGGA        1080
GCCAGGTGTG CCGAGACCAT CCTAAGGGTC CGATCTGACA GCAAGCAAGT GAATAAACAA        1140
TGATTTGCTT TTCAGTGAGA ATATATATAT GAGATATATA TAGATATATA TCTAGGTTGG        1200
GTGGTGGTAG ATCCTTGAGG GTCAGTAGTT TCAAAACCAA AAATATTCTA AGAAGTCTTA        1260
GGATGGAGTT CCTTTTCTTT CTGTTGTTGT TTCCCAGCTA CAACCAACTA AAGACACAAA        1320
TGGCGTTCTG CAAGGGGACT CTGGGAGGAG TTTTCCAGAA TGCAATTCCG AGTGAGCAAA        1380
TCGCATAGCT GTAGAATGTG CGTGCTTTTT TGTGGACACA GGAGCTCCTC CAGGAGCAGG        1440
CTGGGATCCC AACTATCGCT TGTTGCCTCT TTTTCAAGTG GAATTTGAAT TTTAAATAAA        1500
CAACTTTTTT TGGCATGATA AACAGATCAA TAAAAGTTTT GTGAATTCC                    1549
```

(2) INFORMATION FOR SEQ ID NO:2:

(i) SEQUENCE CHARACTERISTICS:
        (A) LENGTH: 343 amino acids
        (B) TYPE: amino acid
        (C) STRANDEDNESS:
        (D) TOPOLOGY: linear (ii) MOLECULE TYPE:
        (A) DESCRIPTION: protein

```
       (iii) HYPOTHETICAL:

(iv) ANTI-SENSE:

(v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:    2:

Val Ser Lys Arg Cys Gly Met Phe Gly Met Gln Gly Asp Val Phe
                 5                  10                  15

Gly Leu Arg Ala His Ser Trp Arg Lys Ile Cys Lys Ser Cys Lys
                20                  25                  30

Cys Ser Gln Glu Asp His Cys Leu Thr Ser Asp Leu Glu Asp Asp
                35                  40                  45

Arg Lys Ile Gly Arg Leu Leu Met Asp Ser Lys Tyr Ser Thr Leu
                50                  55                  60

Thr Ala Arg Val Lys Gly Gly Asp Gly Ile Arg Ile Tyr Lys Arg
                65                  70                  75

Asn Arg Met Ile Met Thr Asn Pro Ile Ala Thr Gly Lys Asp Pro
                80                  85                  90

Thr Phe Asp Thr Ile Thr Tyr Glu Trp Ala Pro Pro Glu Val Thr
                95                 100                 105

Gln Lys Leu Gly Leu Gln Tyr Met Glu Leu Ile Pro Lys Glu Lys
               110                 115                 120

Gln Pro Val Thr Gly Thr Glu Gly Ala Phe Thr Arg Arg Arg Gln
               125                 130                 135

Leu Met His Gln Leu Pro Ile Tyr Asp Gln Asp Pro Ser Arg Cys
               140                 145                 150

Arg Gly Leu Leu Glu Asn Glu Leu Lys Leu Met Glu Glu Phe Val
               155                 160                 165

Lys Gln Tyr Lys Ser Glu Ala Leu Gly Val Gly Glu Val Ala Leu
               170                 175                 180

Pro Gly Arg Val Ala Cys Pro Arg Arg Arg Gly Ser Ser Arg Lys
               185                 190                 195

Ser Gln Arg Gly Gln Arg Pro Leu Leu Leu Pro Pro Thr Ala Val
               200                 205                 210

Ser Val Thr Arg Pro Lys Lys Trp Asn Thr Ser Ala Ser Ser Ala
               215                 220                 225

Arg Glu Arg Pro Leu Leu Thr Ala Pro Trp Ser Thr Arg Gln Gly
               230                 235                 240

Arg Leu Gln Gln Ala Val Ala Pro His Leu Leu Cys Val Cys Gln
               245                 250                 255

Val Leu Arg Ala Ala Gly Gly Pro His Leu Leu Leu Glu Gly Trp
               260                 265                 270

Ser Pro Trp Cys Gly Arg His Tyr Cys Glu Ser Leu Arg Pro Arg
               275                 280                 285

Cys Ser Gly Cys Asp Glu Ile Ile Phe Ala Glu Asp Tyr Gln Arg
               290                 295                 300

Val Glu Asp Leu Ala Trp His Arg Lys His Phe Val Cys Glu Gly
```

```
                         305                 310                 315
Cys Glu Gln Leu Leu Ser Gly Arg Ala Tyr Ile Val Thr Lys Gly
                320                 325                 330
Gln Leu Leu Cys Pro Thr Cys Ser Lys Ser Lys Arg Ser
            335                 340
```

(2) INFORMATION FOR SEQ ID NO:3:

(i) SEQUENCE CHARACTERISTICS:
        (A) LENGTH: 52 amino acids
        (B) TYPE: amino acid
        (C) STRANDEDNESS:
        (D) TOPOLOGY: linear (ii) MOLECULE TYPE:
        (A) DESCRIPTION: protein (iii) HYPOTHETICAL:

(iv) ANTI-SENSE:

(v) FRAGMENT TYPE: internal (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 3:

```
Cys Ser Gly Cys Asp Glu Ile Ile Phe Ala Glu Asp Tyr Gln Arg
                5                   10                  15
Val Glu Asp Leu Ala Trp His Arg Lys His Phe Val Cys Glu Gly
                20                  25                  30
Cys Glu Gln Leu Leu Ser Gly Arg Ala Tyr Ile Val Thr Lys Gly
                35                  40                  45
Gln Leu Leu Cys Pro Thr Cys
                50
```